(12) United States Patent
Mertens et al.

(10) Patent No.: US 6,485,934 B1
(45) Date of Patent: Nov. 26, 2002

(54) REGULATORY SYSTEM FOR INDUCIBLE EXPRESSION OF GENES WITH LAMBDOID PROMOTERS

(76) Inventors: Nico Maurice August Corneel Mertens, Pauwstraat 58, B-9120, Beveren (BE); Eric Rene Remaut, Bergstraat 7, B-9921, Vinderhoute (BE); Walter Charles Fiers, Beukendreef 3, B-9070, Destelbergen (BE)

( * ) Notice: Subject to any disclaimer, the term of this patent is extended or adjusted under 35 U.S.C. 154(b) by 0 days.

(21) Appl. No.: 09/403,651
(22) PCT Filed: Apr. 23, 1998
(86) PCT No.: PCT/EP98/02465
§ 371 (c)(1),
(2), (4) Date: Oct. 22, 1999
(87) PCT Pub. No.: WO98/48025
PCT Pub. Date: Oct. 29, 1998

(30) Foreign Application Priority Data

Apr. 23, 1997 (NL) .............................................. 1005884

(51) Int. Cl.[7] ........................ C12N 15/00; C12N 15/09; C12N 1/21; C12P 21/06; C07H 21/04
(52) U.S. Cl. ................ 435/69.1; 435/320.1; 435/252.3; 435/471; 526/23.1; 530/350
(58) Field of Search ............................. 435/69.1, 320.1, 435/252.3, 471; 536/23.1; 530/350

(56) References Cited

U.S. PATENT DOCUMENTS 5,416,008 A * 5/1995 Bailey et al. ............... 435/69.1
5,571,786 A 11/1996 Eible et al. ..................... 514/8

OTHER PUBLICATIONS

J. Sambrook et al., Molecular cloning, 2nd edition, *Bateriophage Lambda Vectors*, 1987, pp. 2.42–2.43.
David Chapman et al., Engineering proteins without primary sequence tryptophan residues: mutant trp repressors with aliphatic substitutions for tryptophan side chains, *Gene*, vol. 163, 1995, pp. 1–11.

Nico Mertens et al., Tight Transcriptional Control Mechanism Ensures Stable High–Level Expression from T7 Promoter–Based Expression Plasmids, *Bio/Technology*, vol. 13, Feb. 1995, pp. 175–179.

Alexander D. Johnson et al., Lambda Repressor and cro— components of an efficient molecular switch, *Nature*, vol. 294, Nov. 19, 1981, pp. 217–223.

Henry J. George et al., A Bacteriophage Lambda cI857 Cassette Controls Lambda PL Expression Vectors at Physiologic Temperatures, *Bio/Technology*, vol. 5, Jun. 1987, pp. 600–603.

* cited by examiner

*Primary Examiner*—David Guzo
*Assistant Examiner*—Gerald G. Leffers, Jr.
(74) *Attorney, Agent, or Firm*—Knobbe, Martens, Olson & Bear LLP

(57) ABSTRACT

The invention relates to a regulation system for inducible expression of genes, comprising a lambdoid promoter, a gene coding for a repressor for the lambdoid promoter and a gene coding for an antirepressor of the repressor, which antirepressor is under the influence of an inducible promoter. The invention further relates to a regulatory replicon, comprising said gene coding for an antirepressor, an expression system, comprising said regulatory replicon, and an expression vector based on a lambdoid promoter, and also to a method for producing a gene product in a heterologous host, by providing a culture of a host comprising a heterologous sequence which codes for the gene product. Providing a culture of a host comprising a heterologous sequence is obtained by putting the expression of the heterologous sequence under the control of a regulation system, a gene coding for a repressor for the lambdoid promoter and a gene coding for an antirepressor, and by inducing the promoter of the antirepressor gene.

13 Claims, 19 Drawing Sheets

SEQUENCE LISTING

```
<160> NUMBER OF SEQ ID NOS:   4

<210> SEQ ID NO 1
<211> LENGTH: 32
<212> TYPE: DNA
<213> ORGANISM: Artificial Sequence
<220> FEATURE:
<223> OTHER INFORMATION: P22 ant forward primer.

<400> SEQUENCE: 1
atcagaattc gcggtaacag tcagggcttc gg                                32

<210> SEQ ID NO 2
<211> LENGTH: 31
<212> TYPE: DNA
<213> ORGANISM: Artificial Sequence
<220> FEATURE:
<223> OTHER INFORMATION: P22 ant backward primer.
```

-continued

```
<400> SEQUENCE: 2
ttaaggatcc gaagctgggt cgttgcgttg g                              31

<210> SEQ ID NO 3
<211> LENGTH: 38
<212> TYPE: DNA
<213> ORGANISM: Artificial Sequence
<220> FEATURE:
<223> OTHER INFORMATION: NM73 primer for amplifying the ParaBAD promoter
      and araC repressor gene from E.coli K12.

<400> SEQUENCE: 3
atatatccaa ggttatgcaa tcgccatcgt ttcactcc                       38

<210> SEQ ID NO 4
<211> LENGTH: 34
<212> TYPE: DNA
<213> ORGANISM: Artificial Sequence
<220> FEATURE:
<223> OTHER INFORMATION: NM72 primer for amplifying the ParaBAD promoter
      and araC repressor gene from E.coli K12.

<400> SEQUENCE: 4
atatcggccg ttatgacaac ttgacggcta catc                           34
```

REGULATORY SYSTEM FOR INDUCIBLE EXPRESSION OF GENES WITH LAMBDOID PROMOTERS

This is U.S. National phase under 35 U.S.C. § 371 of International Application PCT/EP98/02465, filed Apr. 23, 1998, which claims priority of the Netherlands application 1005884, filed April 1997.

FIELD OF THE INVENTION

The present invention relates to a new regulatory system for inducible expression of genes based on lambdoid promoters. The invention further relates to a regulatory replicon and a method for producing heterologous proteins.

BACKGROUND OF THE INVENTION

In order to enable production of human or animal proteins in sufficient quantities, the gene which codes for the protein is usually cloned in the bacteria *Escherichia coli*. This bacteria has a high synthesis capacity and is well characterized at molecular level. Bacterial regulation signals are also required for expression of the cloned gene in the bacterial host.

It has been found that the strongest regulation signals for *E. coli* do not originate from the bacteria itself but from the bacteria-challenging bacteriophages. There exist so-called non-temperate and temperate phages.

The first type are the phages with unregulated promoters. Genes under the control of such promoters are continuously expressed. This results in a high protein production, which can be detrimental or even lethal to the host bacteria.

The other type, the so-called temperate phages, can insert their DNA in a non-active form in the host genome and therefore co-replicate passively with this host genome. By induction of particular promoters the host is stimulated to produce phage protein or, in the case of expression vectors based on phage promoters, to produce the heterologous protein. As long as there is no induction, expression from the promoter is shut off by means of repressor molecules binding cooperatively to the promoter. The promoters of temperate phages are among the strongest, but also the best expressed and controllable promoters from *E. coli* known (Lanzer & Bujard (1988); Knaus & Bujard (1988)).

The combination of intrinsic strength and superior regulation make these promoters preferable to other regulated or non-regulated *E. coli* promoters for obtaining heterologous expression on industrial scale.

The best known and prototype phage from the group of temperate phages is the *E. coli* phage λ. There are many λ-related or lambdoid phages such as 21, φ80, φ81, 82, 424, 434, P22, etc. These phages usually have a different immunity, inter alia through the use of different promoter sequences, repressor molecules and operator sequences.

Many expression plasmids for heterologous protein production which are used in *E. coli* based on the λ$P_L$ promoter. The λ$P_L$ promoter is very strong and can be well regulated. The best known and most controllable regulation mechanism makes use of a thermosensitive mutant of the original repressor molecule. Induction of protein synthesis from the promoter can in this case be started by increasing the temperature from 28° C. to 42° C. The repressor molecule is deactivated by this temperature increase. However, this higher temperature can also be unfavorable for production of many proteins because the protein, instead of remaining soluble, then precipitates for the greater part in the form of so-called inclusion bodies, wherein it loses its activity.

Inclusion bodies are in fact an aggregate of incorrectly folded polypeptide chains. It is a phenomenon which is observed on both laboratory scale and industrial scale when an attempt is made to produce large quantities of a specific protein in *E. coli*. Inclusion bodies can per se be separated quite easily from the other cellular proteins in one step. However, after isolation of the inclusion bodies the protein must first be denatured by means of for instance urea or guanidine hydrochloride and then slowly refolded into the natural spatial structure. This refolding of the protein from inclusion bodies is not always successful and generally results in a considerable loss of material and entails extra costs in the scale-up process due to an increase in the number of steps in the final processing. The frequent occurrence of inclusion bodies has resulted in it not always being possible to fully utilize the potential of an economically advantageous expression host for heterologous protein production.

It has been found that the formation of inclusion bodies can sometimes be prevented by reducing the fermentation temperature. The reason therefor may be either that the lower temperature has a different effect on the folding of the overproduced protein or that there are fewer newly synthesized protein molecules per unit of time and volume.

When protein synthesis at a lower temperature is desired, it is no longer possible to use the currently existing and much used temperature induction in combination with the strong and well regulated promoters derived from phage lambda and related promoters.

BRIEF SUMMARY OF THE INVENTION

It is therefore the object of the present invention to provide a simple, well controllable regulation system for strong and highly repressible promoters derived from lambdoid phages, with which induction at a lower temperature becomes possible.

This is achieved by the invention with a regulation system for expression vectors, comprising a lambdoid promoter, a gene coding for a repressor for the lambdoid promoter and a gene coding for an antirepressor of the repressor, which antirepressor gene is under the control of an inducible promoter. This promoter can originate from a. gene other than the antirepressor gene itself and is preferably inducible at lower temperatures.

The regulation of the heterologous protein expression can now be controlled by the expression of the antirepressor. The absence or presence of the antirepressor determines the suppression or activation, respectively, of the promoter of the protein to be produced. The presence or absence of the antirepressor is in turn regulated by whether or not the promoter of the antirepressor is induced.

Regulation of the antirepressor gene can occur in different ways. Use can thus be made for instance of a promoter regulatable by lactose, arabinose or the absence of amino acids or of any other regulatable promoter.

The different components of the regulation system according to the invention can be located on the chromosome of the host as well as on one or more individual replicons, such as plasmids. In a particular embodiment the antirepressor gene can lie on a regulatory plasmid together with the gene coding for the repressor of the promoter of the antirepressor gene. Such a regulatory plasmid can then be combined with any random expression vehicle containing the heterologous gene and its promoter and repression system. Optionally the repression system of the promoter of the heterologous gene can also be situated on the regulatory vehicle. All components can also lie on different replicons.

In a preferred embodiment of the invention the antirepressor is the ant of the lambdoid phage P22. Ant is coded in the immI region of phage P22 from *Salmonella typhimurium* and engages in a non-covalent interaction with the C-terminal part of the P22c2 repressor and thereby prevents the dimerization of the c2 repressor required for repressor activity and thereby binding to the operator.

In a preferred embodiment of the regulation system according to the invention the expression of this antirepressor is under the control of an inducible promoter such as $P_{N25/O2}$. Repression of the $P_{N25/O2}$ promoter takes place for instance by means of the lacI repressor of *E. coli*. The induction of this promoter is based on derepression and preferably takes place by means of administering IPTG.

The regulation system according to the invention is a flexible system wherein according to a preferred embodiment the induction of the desired heterologous protein synthesis can take place in two ways. On the one hand the production of the antirepressor can already be initiated at low temperature by adding IPTG, which leads to derepression of the lambdoid promoter. It is also possible to use the same bacterial culture, wherein the conventional temperature-dependent induction can still be applied.

The regulation system can be applied with any expression vector derived from lambda. As regulatable promoter of the heterologous gene the $\lambda P_L$ promoter is particularly recommended, but the invention is certainly not limited thereto. The $\lambda P_R$ promoter or any lambdoid promoter which can be repressed by a repressor with sufficient homology in the C-terminal region to P22c2 to be recognized by ant can also be used.

The principle of the invention, i.e. regulating a promoter inducible by a repression system by means of an antirepressor to be expressed in regulated manner, can of course also be applied within the scope of the present invention in configurations other than those specifically described herein.

The invention further relates to a regulatory replicon, comprising a gene coding for an antirepressor, which antirepressor gene is under the control of an inducible promoter. The replicon can further comprise a gene coding for a repressor of the inducible promoter of the antirepressor gene. A gene which codes for a repressor for a lambdoid promoter can moreover also be present in the replicon.

In a preferred embodiment a replicon according to the invention comprises the gene coding for the P22ant protein of *S. tyohimurium*, under the control of the $P_{N25/O2}$ promoter, the lacI$^q$ gene under the control of the pLacI$^q$ promoter and the gene coding for the cI857 repressor.

A preferred embodiment of a regulatory replicon according to the invention is shown in FIGS. 1 and 3. Both figures show the plasmid, designated herein pICA2. FIG. 3 shows the general structure and FIG. 1 the restriction map. The construction of this plasmid is described in the examples.

In an alternative embodiment of the replicon according to the invention the replicon can further comprise the regulation signals, including the lambdoid promoter, required for expression of a heterologous gene.

In such an embodiment there are not therefore two separate vectors for expression and regulation, but only one.

The invention moreover relates to an expression system, comprising a regulatory replicon and an expression vector derived from phage lambda. Examples of expression vectors derived from phage lambda are pLT10T or pLR10T.

Finally, the invention relates to a method for producing a gene product in a heterologous host, comprising providing a culture of a host comprising a heterologous sequence which codes for the gene product, wherein the expression of the heterologous sequence is under the control of a regulation system which at least consists of a lambdoid promoter operably linked to the heterologous sequence, a gene coding for a repressor for the lambdoid promoter and a gene coding for an antirepressor, which antirepressor gene is operably linked to an inducible promoter, and of inducing the promoter of the antirepressor gene. If the inducible promoter of the antirepressor gene is the $P_{N25/O2}$ promoter, it can be induced by adding IPTG to the culture.

DETAILED DESCRIPTION OF THE PREFERRED EMBODIMENTS

Figure 1A:
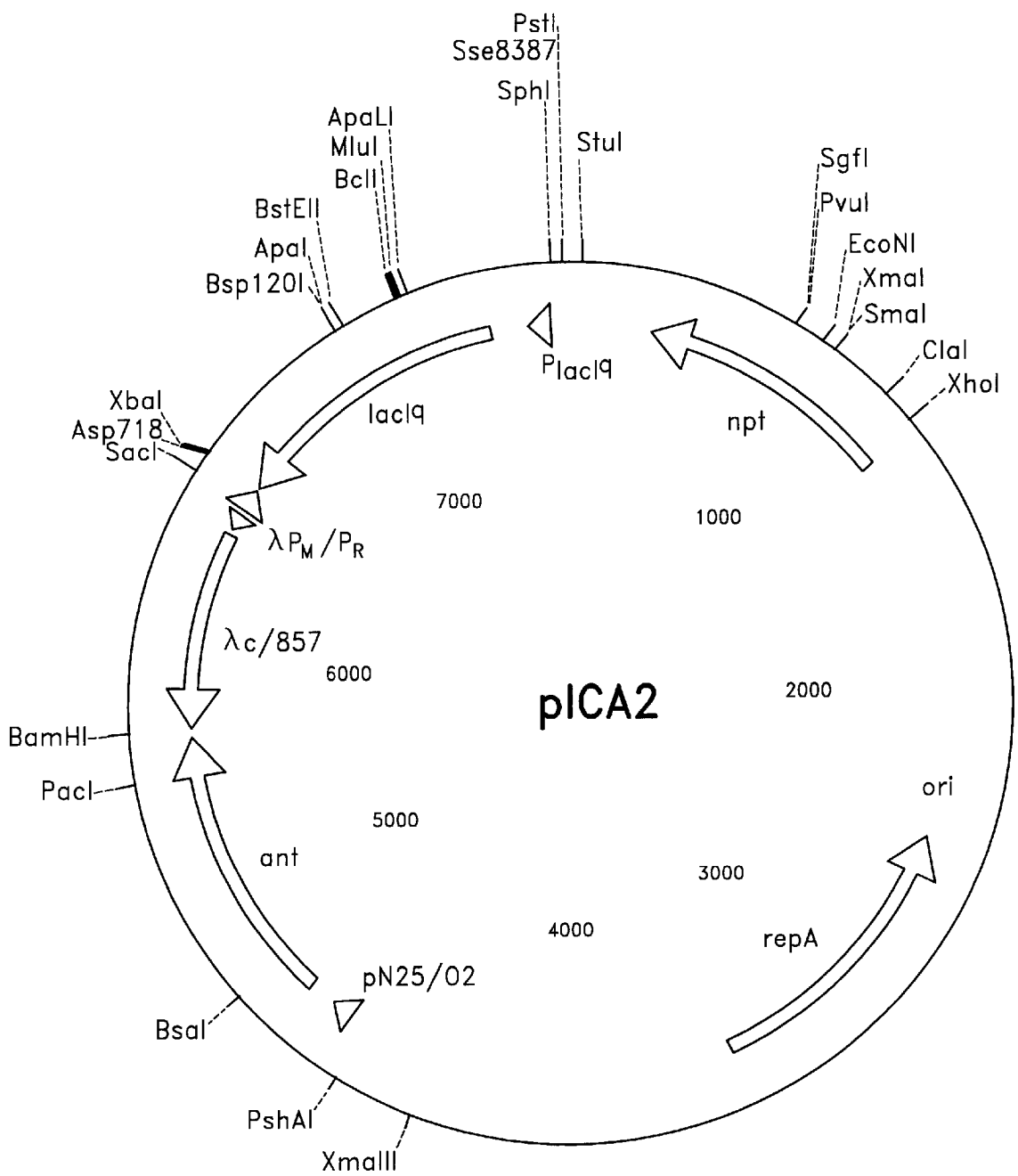
FIG. 1A: Schematic drawing of the pICA2 plasmid comprising the lactose repressor gene (lacI) controlled by the lacIq promoter, the thermosensitive lambda repressor gene (cI857) controlled by the lambda PM promoter (overlapping the opposite oriented PR promoter), and the P22 antirepressor gene (ant) fused to a promoter that is controlled by the lactose repressor (PN25/O2). The plasmid further comprises the low-copy replication origin derived from pLG339, and a neomycin phosphotransferase gene (npt) for kanamycin resistance. Some restriction enzyme recognition sites are indicated.

Following below is a summary of the definitions used in this application.

Antirepressor: protein which can neutralize a repressor and thus activates the repressed promoter.

Phage: (bacteriophage) a virus whose host is a bacteria.

Phage λ: (bacteriophage lambda) temperate bacteriophage which infects *Escherichia coli*, belongs to the Stylovirudae family.

Phage P22: (bacteriophage P22) temperate phage which infects *Salmonella typhimurium*, belongs to the Podoviridae family.

Gene Expression: expression of a gene by transcription and translation to a polypeptide or a protein (functional protein).

Temperate Phage: phage which can pass on its genetic information through infection as well as via the cell division of the host after insertion in the genome.

Immunity: (phage immunity) superinfection resistance for phages with the same or homologous regulatory elements.

Inclusion Bodies: discrete structures consisting of non-native folded, coagulated protein.

LMBP: Laboratory of Molecular Biology Plasmid collection, recognized deposit body for plasmids, part of the Belgian Coordinated Collection of Micro-organisms (BCCM).

Plasmid: extra-genomic replication unit.

Promoter: DNA sequence which allows transcription to initiate.

Replicon: a unit of DNA replication.

Repressor: protein which prevents transcription initiation on one or more determined promoters.

Vector: a biological entity which can ensure the multiplication of genetic information.

In the examples below the invention is illustrated on the basis of the prokaryote lacZ gene and the eukaryote genes coding for human interferon-γ (hIFN$_\gamma$), murine Interleukin 2 (mIL2) and human Interleukin 2 (hIL2) as model system for protein synthesis. It will be apparent to a person skilled in the art that in an analogous manner other genes can be expressed in a regulated manner with the system described here without any inventive work having to be performed for this purpose.

EXAMPLES

The materials and methods used are first elucidated hereinbelow. Thereafter the invention is illustrated in the examples. In support of most of the methods reference is further made to Sambrook et al. (1989) Molecular cloning: a Laboratory Manual, 2nd ed. Cold Spring Harbor Laboratory Press, Cold Spring Harbor, USA, and Miller, J. (1972) Experiments in Molecular Genetics, Cold Spring Harbor Laboratory, New york.

MATERIALS AND METHODS
1. Bacteria Strains, Phages and Plasmids

All cloning experiments were carried out in *E. coli* MC1061 (hsdR mcrB araD139 Δ(araABC-leu)7697 ΔlacX74 galU galK rpsL thi) (Casadaban and Cohen, 1980) lysogenized with λ when multiplying λP$_L$-containing plasmids. Expression experiments were carried out in MCI061 transformed with a regulatory plasmid (for instance pcI857 or pICA2).

The repressor came from pcI857 (LMBP537), a vector with a high copy number (P15A replicon), which carries an autogenously regulated cI857 gene coding for a thermosensitive cI mutant (Remaut et al., 1983).

Figure 1B:
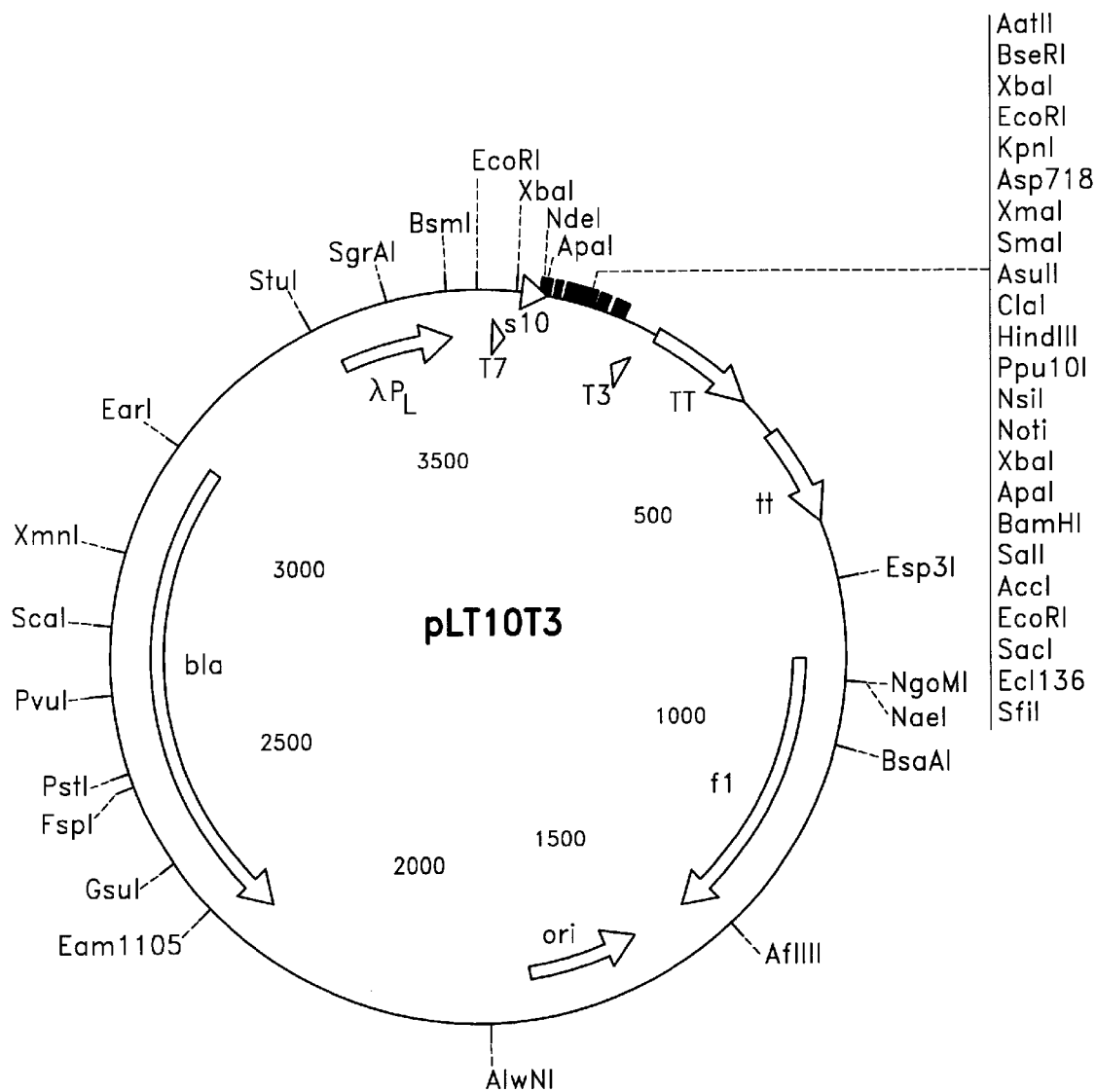
FIG. 1B: Schematic drawing of a typical expression plasmid that can be used in combination with the antregulatory system. The pLT10T3 plasmid comprises the lambda PL promoter, a T7 promoter, an antisense T3 promoter, a suitable ribosomal binding site (s10) derived from phage T7 gene 10 (T7g10), a multiple cloning site, a tandem transcription terminator for the T7 RNA polymerase (TT) and a tandem transcription terminator for the *E. coli* RNA polymerase (tt). The plasmid further comprises an f1 replication origin, a plasmid replication origin derived from the high-copy number plasmid ColE1, and a β-lactamase encoding gene for ampicilin resistance.
Figure 1C:
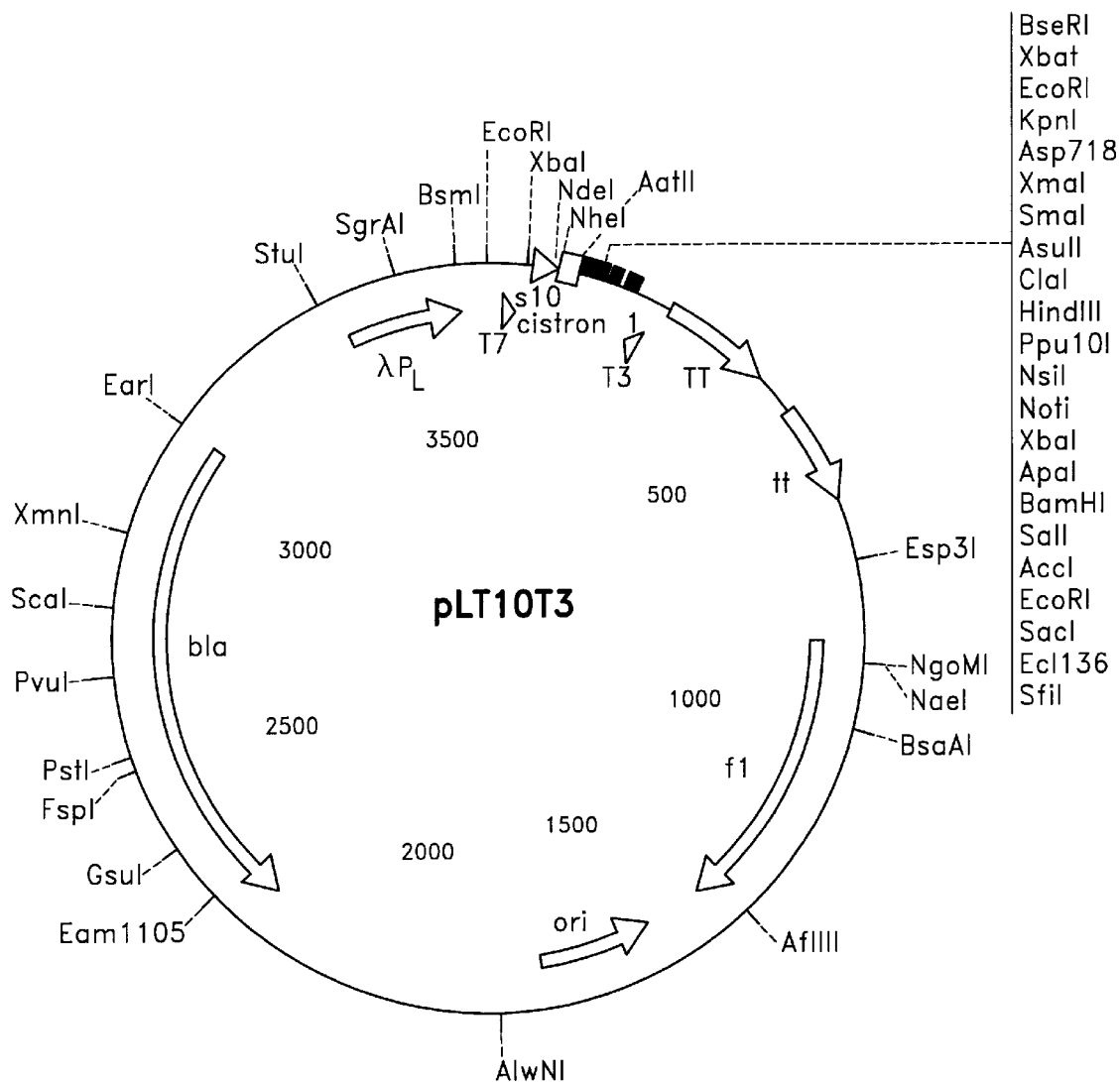
FIG. 1C: Schematic drawing of a derivative of the expression vector pLT10T3, where the heterologous gene is to be fused to a first translated cistron, instead of fusing to the T7g10 ribosomal binding site (s10).
Figure 2:
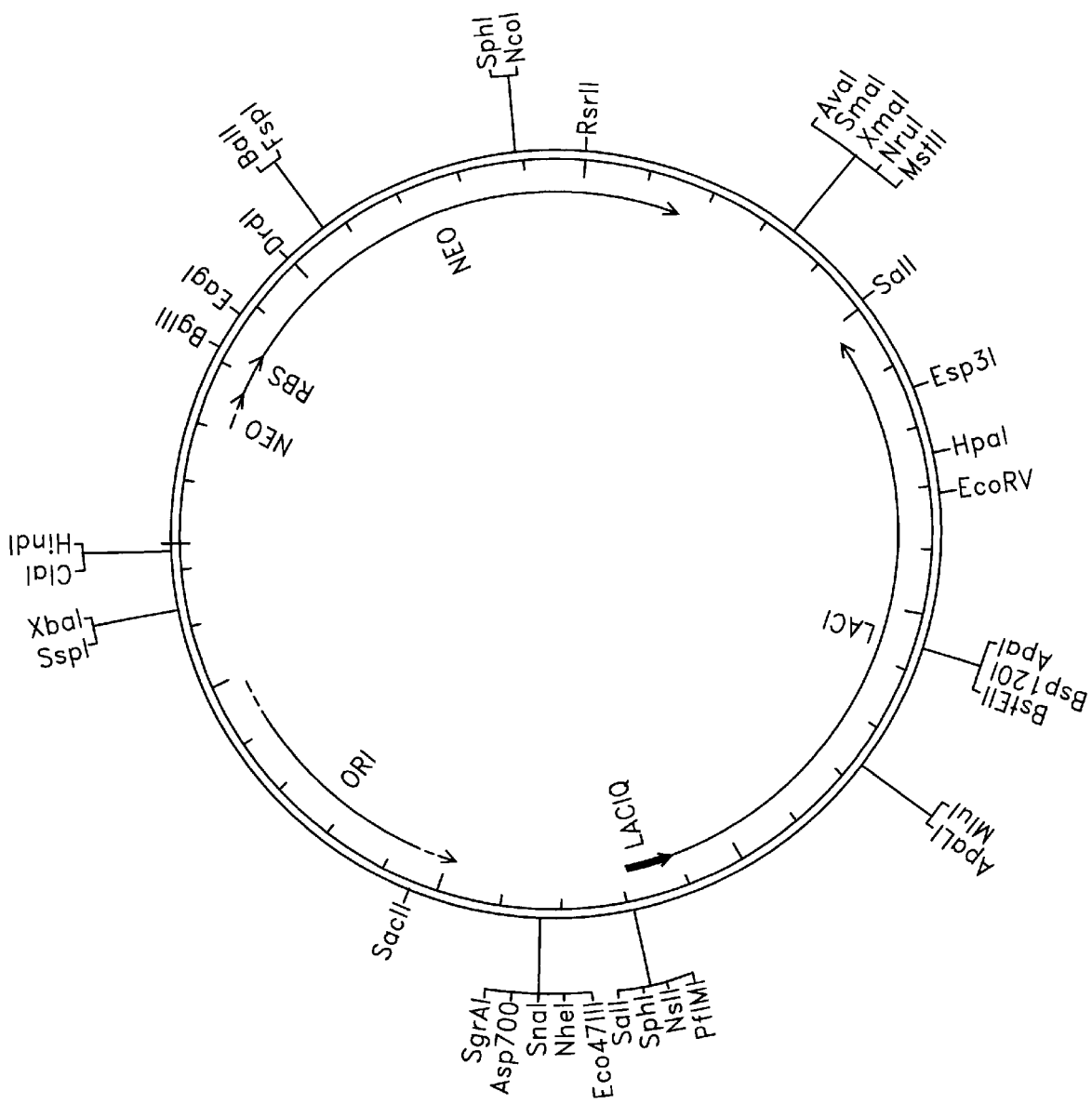
FIG. 2: Schematic drawing of the pDMI,1 regulatory plasmid, comprising the lactose repressor gene controlled by the PlacIq promoter. The plasmid further comprises a neomycin resistance gene (neo) and a plasmid replication origin of the P15A replication origin classification, allowing an intermediate copy number.

*S. typhimurium* LT2 (ATCC 19 585) was grown in Nutrient Broth (Difco 0001) supplemented with 0.5% NaCl. Phage P22 (ATCC 19 585-B1) stocks were obtained from confluent lysis plates prepared by using an excess of plaque-forming units with freshly prepared nutrient agar plates. The macerated soft agar was cleared by centrifugation to isolate the phage particles. P22 DNA was prepared by phenol extraction of purified phage particles.

pLR10T is a vector derived from pLt10T (Mertens et al., 1995 B) in which the actual translation initiation site is preceded by a small, well-translated cistron which resulted from a fusion of the N-terminal region of T7g10 and the C-terminal piece of the *E. coli* trpB gene (FIG. 1).

pDMI,1 (LMEP1594) was obtained from Dr. Dietrich Stüber (Hoffman-La Roche, Basel, Switzerland). (See FIG. 2)

Figure 3A:
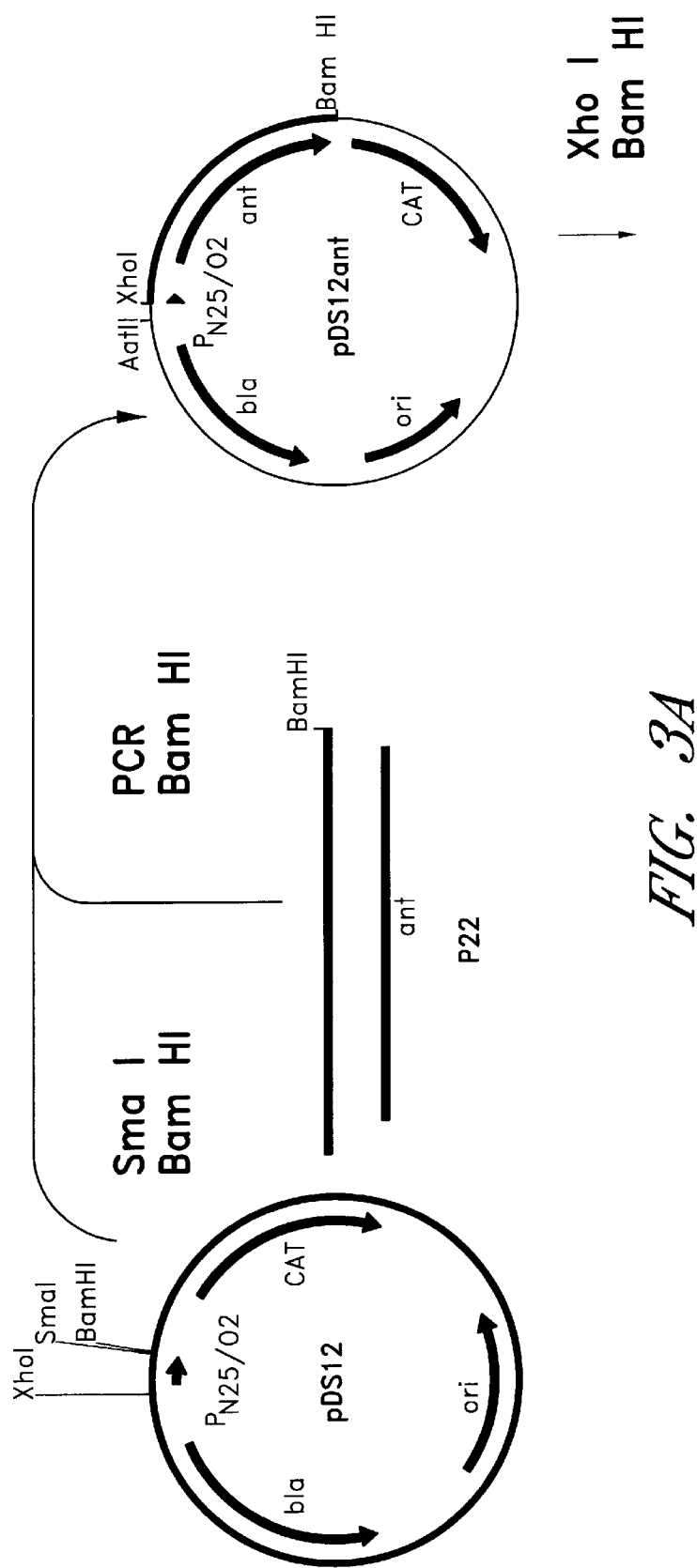
FIG. 3A. Construction scheme of the pICA2 plasmid. The P22ant gene was cloned in pDS12 digested with the restriction enzymes SmaI and BamHI, giving rise to pDS12ant.
Figure 3B:
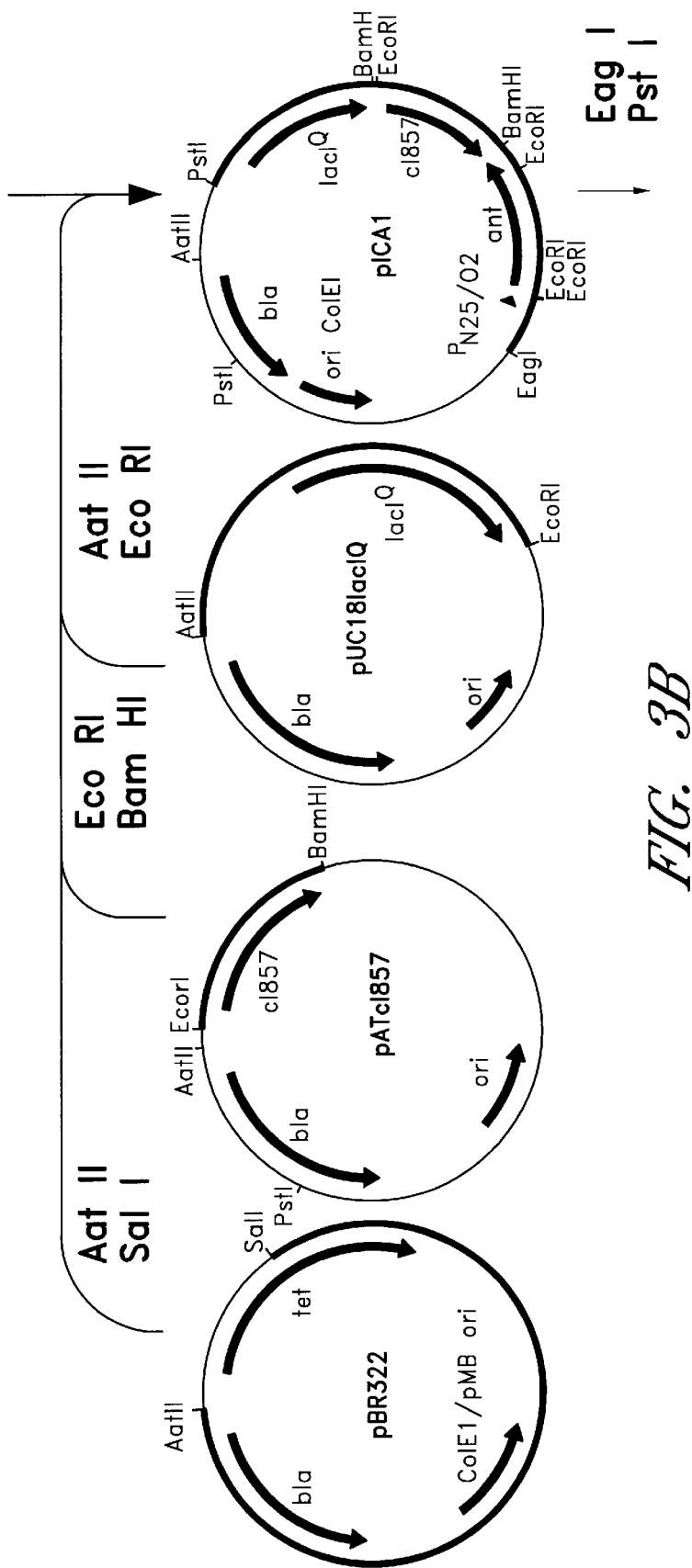
FIG. 3B: In a next step the vector fragments indicated with a bold line derived from pBR322 (SalI, AatII), pATcI857 (EcoRI, BamHI) and pUC18lacIq (AatII, EcoRI) were combined and ligated to give rise to pICA1.
Figure 3C:
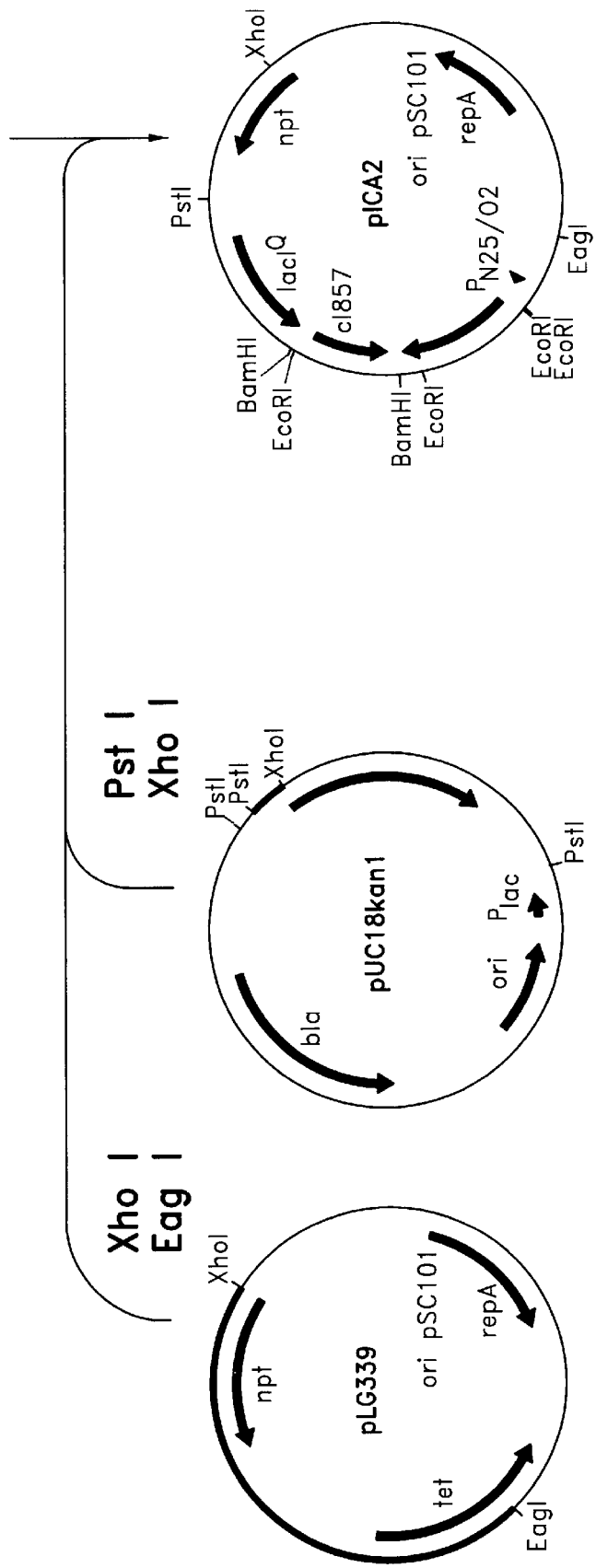
FIG. 3C: The fragment indicated with a bold line in pICA1 was isolated with the restriction enzymes PstI and EagI and combined with the vector fragments indicated in bold from pLG339 (EagI, XhoI) and pUC18kan1 (PstI, XhoI) to give rise to pICA2.

2. Plasmid Construction (FIG. 3)

Plasmid DNA purification was carried out as described in Sambrook et al., 1989. All enzymes used for plasmid cloning were obtained from New England Biolabs or Boehringer Mannheim and used according to the recommendations of the supplier.

The P22 ant region was amplified by means of PCR with Vent DNA polymerase (New England Biolabs) using 5'-ATCAGAATTCGCGGTAACAGTCAGGGCTTCGG-3' (SEQ. ID NO: 1) and forward and 5'-TTAAGGATCCGAAGCTGGGTCGTTGCGTTGG-3' (SEQ. ID NO: 2) as backward primer. This amplifies a 1054 bp DNA region spanning the coordinates 498–1531 of the POP22IMM Genbank sequence (Sauer et al., 1983). This includes the ant coding region with its own ribosomal binding site and adds a BamHI restriction site to the 3' end.

The amplified fragment was trimmed with BamHI and ligated in a pDS12 vector opened with SMaI and BamHI (Stüber et al., 1984). An XhoI-BamHI fragment from pDS12ant (with the PN$_{25/O2}$-ant combination) was combined with the cI857 gene on an EcoRI-BamHI fragment derived from pAT153cI857 (Mertens et al., 1995 A), (LMBP1065), a lacI$^q$-containing fragment from pUC18lacI$^q$ (LMBP3259) trimmed with AatII and EcoRI, and an AatII-SalI pBR322 (LMBP140) vector part. The resulting pICAl is a multi-copy number plasmid which contains a combination of lacI$^q$, cI857 and P$_{N25/O2}$ ant which is useful according to the invention. From this plasmid an EagI-PstI fragment was combined with a pUC18Kan (Pharmacia, Sweden) trimmed with PstI and XhoI and containing an npt gene (Km$^R$ (kanamycin resistance)) and an XhoI-EagI vector fragment from pLG339 (Stoker et al., 1982) in order to obtain the plasmid pICA2 according to the invention. pICA2 (FIG. 1) is a low copy number plasmid compatible with all current expression vectors in respect of replication origin (pSC101) and antibiotic selection.

3. Gene Induction and Protein Analysis

Expression strains containing pCI857, pICA1 or pICA2 were kept at a non-permissive temperature (28° C.). during manipulations preceding induction. λP$_L$-dependent temperature induction was carried out in MC1061 with either pICA2 according to the invention or the known pcI857 by raising the culture temperature from 28° C. to 42° C. MC1061 (pICA1) and MC1061 (pICA2) were induced at temperatures of 28° C. or lower by adding IPTG to a final concentration of 1 mM. The cells were harvested, resuspended in sonication buffer (SB, 10 mM Tris-Cl pH 7.5; 0.1 M NaCl; 5 mM DTT; 10% glycerol) and frozen at −20° C. Aliquots (usually 200 μl) were thawed at 37° C. and cooled on ice. The cells were subsequently opened by sonication on ice using a Sonics & Materials (Danbury Conn., USA) sonicator with a microtip. Lysates were then cleared by centrifugation at 15 000 G for 15 minutes.

Prior to cytokine assay the lysates were diluted in SB and filtered over a cellulose-acetate 0.22 μm pore-size filter.

β-Galactosidase was assayed using ONPG as substrate (Miller, 1972).

mIL2 titers were determined by a proliferation assay using the IL2-dependent cytotoxic T-cell line CTLL-2 (Guisez et al., 1993).

Human interferon-γ activity was determined on human FS4 cells by a cytopathic effect reduction assay using encephalomyocarditis virus as challenge virus (Devos et al., 1982).

Example 1

Construction of a Regulatory Plasmid for IPTG Induction of λP$_L$

The ant gene of phage P22 of *S. typhimurium* was amplified from purified P22 DNA and cloned in the pDS12 expression vector, as described in Materials and Methods. In this manner the gene was under the control of the $P_{N25/O2}$ promoter (Strueber et al., 1984) inducible by means of IPTG. Induction of the resulting expression plasmid pDS12 ant resulted in a high production of the repressor P22 ant (FIG. 4B).

The ant gene was subsequently combined with $lacI^q$ and λcI857 in a manner such that the different promoters did not interfere with the expression of each individual gene. The resulting combination (pICA1) was transferred to a low copy number replicon which is ColE1-compatible and derived from pSC101 and also carried a kanamycin resistance selection marker (Stoker et al., 1982). The resulting plasmid pICA2 contains all necessary information for repression of $\lambda P_L$ or $\lambda P_R$ (by means of cI857) and repression (by means of $lacI^q$) and induction (from the $P_{N25/O2}$-ant promoter) of the antirepressor, and can therefore be used as a suitable expression regulatory plasmid for IPTG-induced $\lambda P_L$ or $\lambda P_R$ expression when it is combined with an expression plasmid containing a gene under the transcriptional control of the $\lambda P_L$ or $\lambda P_R$ promoter.

Example 2

Tight Regulation and Expression at Low Temperatures with the P22 Ant-based Expression System In order to quantify the characteristics of the new expression system an expression vector was used containing as model gene a $\lambda P_L$-driven lacZ gene for protein synthesis. This vector is capable of inducing high levels of functional B-galactosidase by means of translationally-coupled translation initiation (Mertens et al., 1995 A; Mertens et al., 1997).

The non-induced levels of B-galactosidase, which could be influenced by a possible continuous presence of low non-induced levels of antirepressor protein, were comparably low when pICA2 or pcI857 (without antirepressor) plasmid were used. This means therefore that low, non-induced levels of antirepressor protein are probably not present, since if this were indeed the case a higher expression of lacZ would be expected.

Figure 4A:
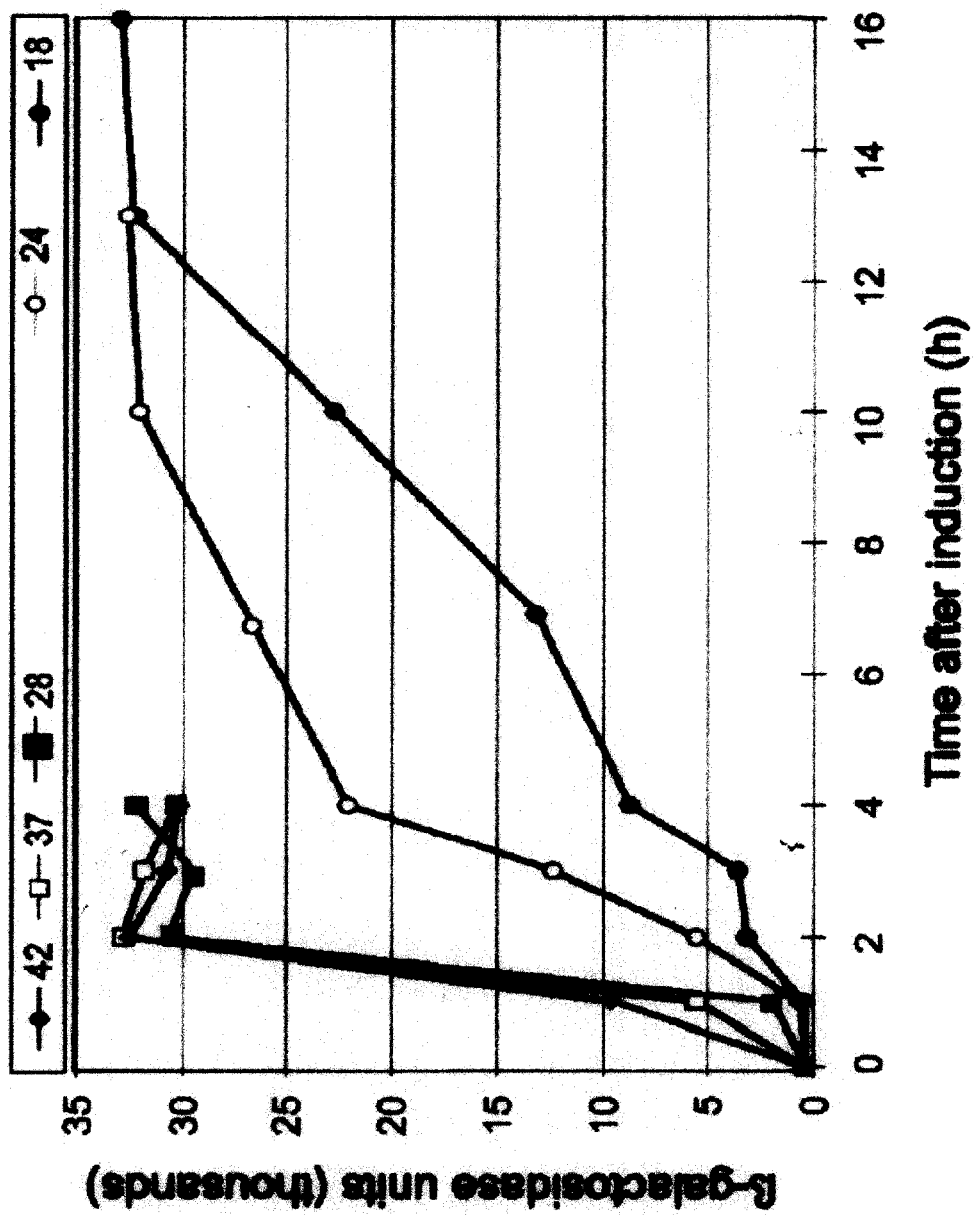
FIG. 4A: Kinetics of β-galactosidase production at different growth temperatures from $\lambda P_L$ by induction of ant from pICA2 following addition of 1 mM IPTG. All cultures eventually reach the same plateau-value of maximal enzyme expression. Due to the use of the thermo-sensitive cI857 repressor, temperatures above 28° C. also result in thermo-induction. At temperatures below 37° C., *E. coli* metabolism and growth rate are dramatically reduced.
Figure 4B:
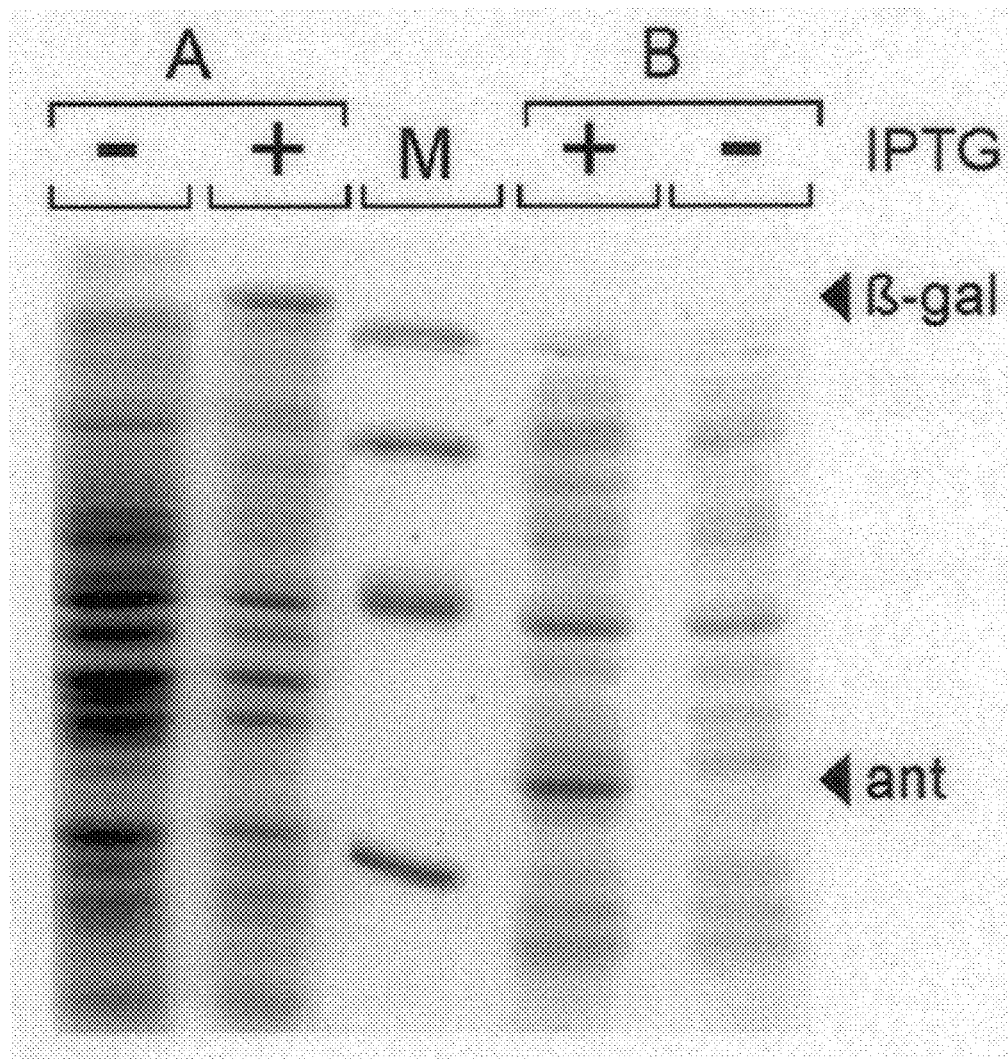
FIG. 4B: A represents the proteins of MC1061[pICA2] [pLR10βGal] before (−) and after (+) the addition of IPTG at 28° C. B compares protein extracts from induced (−) and non-induced (+) MC1061[pDMI,1][pDS12ant], also by the addition of IPTG. The positions of the Ant protein and of β-galactosidase are indicated by arrows. Lane M represents the marker proteins with a molecular mass of 94; 67; 43 and 30 kDa.

Investigation of the induction kinetics of the lacZ gene was carried out in MC1061[pICA2] at 18° C., 24° C., 28° C., 37° C. or 42° C. after adding 1 mM IPTG (FIG. 4A). Temperatures above 28° C. likewise denature the temperature-sensitive cI857 λ-repressor and are an indication of the level of expression obtainable with this vector by thermo-induction. From FIG. 4A can be concluded that maximum B-galactosidase levels can be obtained by adding IPTG at lower temperatures. As expected, the induction kinetics were slower at temperatures under 28° C., because under these sub-optimal growth conditions a lower growth rate and a lower metabolism are obtained.

FIG. 4B compares the level of the induced proteins in MC1061[pICA2] [pLR10βgal] and MC1061[pDMI,1] [pDS12 ant], which shows that the high expression level of P22 ant obtained using the high copy number expression vector pDS12 ant disappears by transferring the $P_{N25/O2}$-ant combination to a low copy number plasmid (6–10 copies/ cell), while still retaining the ability to induce the lambdoid promoter by induction of ant.

Decreasing the synthesis of the repressor antagonist to <1% of the total protein synthesis is advantageous because the ultimate concern is to obtain a large quantity of a particular protein—the gene of which has been inserted behind the strong lambdoid promoter—and the ultimate yield of this target protein can be adversely affected if the repressor antagonist must be produced in large quantities.

Example 3

Induction at Low Temperature can Improve the Production of Soluble Heterologous Proteins Induction resulting in a high expression level, particularly at increased temperatures where the *E. coli* metabolism is high, often results, as already indicated above, in the production of inclusion bodies, while at the same time further cell growth is often inhibited. For reasons which are still not entirely clear, induction at low temperatures is more favourable when production of correctly folded, soluble protein is required. (Lin et al., 1990; Shirano & Shibata, 1990; Schein and Noteborn, 1988; Bishia et al., 1987; Mizukami et al., 1986).

This example therefore investigates whether the different methods of induction (temperature increase or IPTG) result in different quantities of soluble protein.

Used for this purpose were expression vectors derived from pLt10T (Mertens et al., 1995) containing one of the following genes: prokaryotic T7g10 or thioredoxin, two proteins which can be readily expressed in *E. coli*); human interferon-γ (hIFNγ) and murine interleukin-2 (mIL2).

Figure 5A:
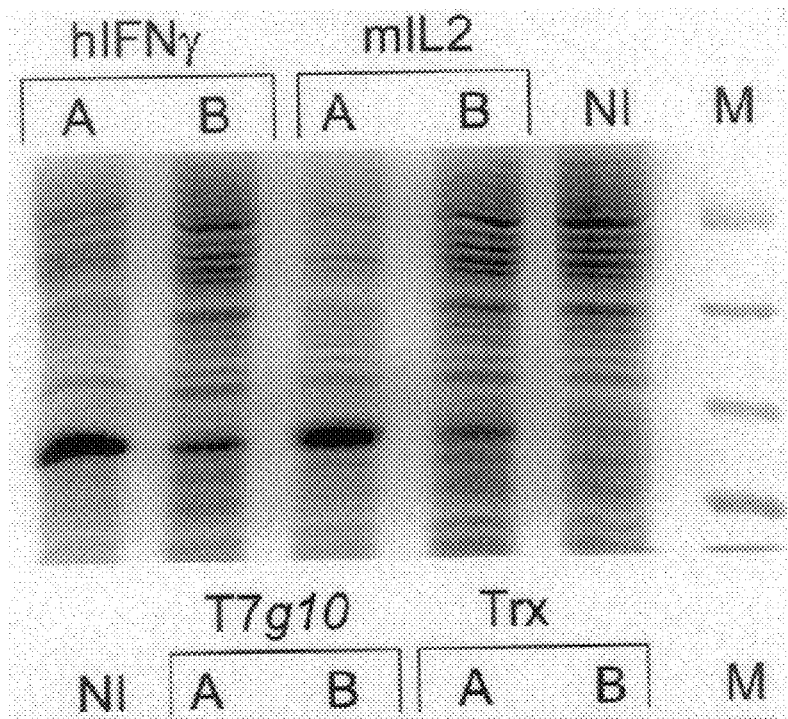
FIG. 5A: Coomassie Brillant Blue stained protein gel comparing the total protein content of cells induced by thermo-induction at 42° C. (A) or IPTG induction at 28° C. (B). In the first two lanes the induction of human interferon gamma is compared, the two following lanes compare the induction of murine interleukin 2. The fifth lane contain a non-induced protein extract and the last lane contains marker proteins to calibrate the gel.
Figure 5B:
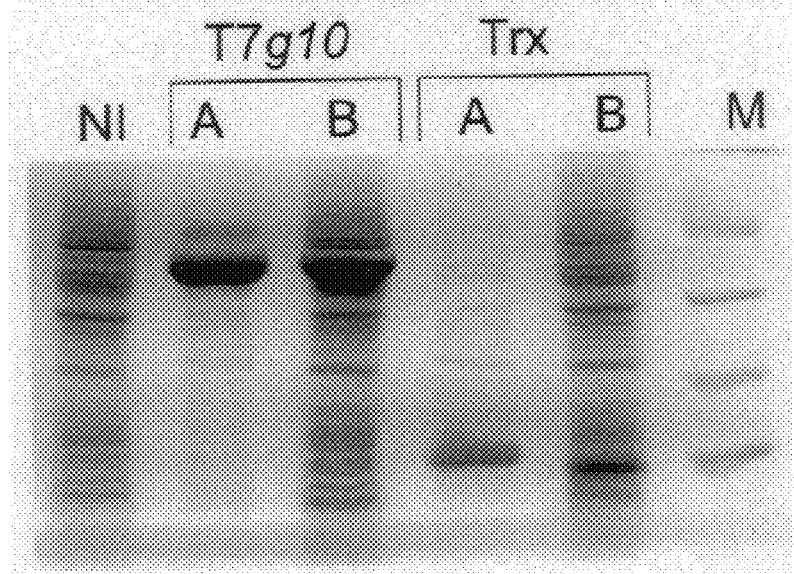
FIG. 5B: Coomassie Brillant Blue stained protein gel comparing the total protein content of cells induced by thermo-induction at 42° C. (A) or IPTG induction at 28° C. (B). In the first two lanes the induction of T7 gene 10 is compared, the two following lanes compare the induction of *E. coli* thioredoxin. The fifth lane contains a non-induced protein extract and the last lane contains marker proteins to calibrate the gel.

FIG. 5 compares production levels obtained either after thermo-induction or after low temperature IPTG induction. It can be clearly inferred from the prokaryotic examples, T7g10 and thioredoxin, that in the same time-span the same quantity of heterologous protein can be induced. The strains induced by means of IPTG continued to grow and eventually synthesized a larger quantity of host proteins (FIG. 5B, lane B). This resulted in a lower yield in comparison with the total protein content (% of the total protein), but gave practically the same absolute yield (mg protein per liter culture). In the figure equivalent quantities of bacterial cultures are compared to each other.

FIG. 6 shows the activities of mIL2 and hIFNγ obtained after induction by temperature increase or by IPTG induction.

Figure 6A:
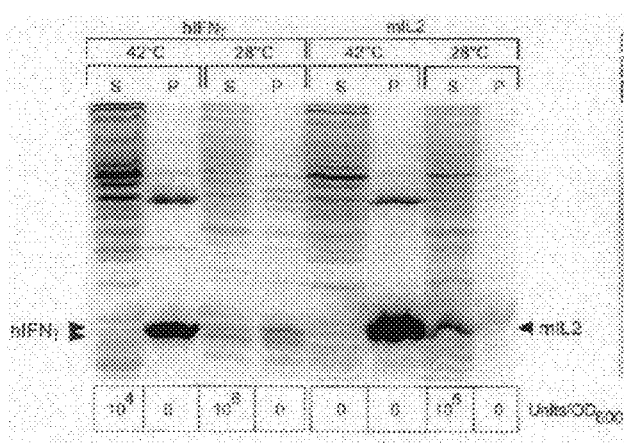
FIG. 6A: Coomassie Brillant Blue stained protein gel comparing the soluble and non-soluble fractions from *E. coli* expression strains producing human interferon gamma (hIFNγ) or murine interleukin 2 (mIL2). The presence of both induced proteins is indicated by arrow points. The bottom row indicated the biological activity found in the cell extracts as titrated with a specific assay for the respective protein.
Figure 6B:
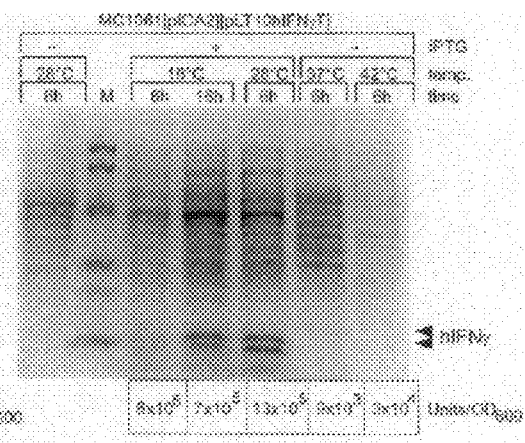
FIG. 6B: Coomassie Brillant Blue stained protein gel comparing only the soluble phase of protein extracts from expression strains induced to produce human interferon gamma (hIFNγ) at different temperature (18° C., 28° C., 37° C. and 42° C.) for either 6 h or 16 h. The with M contains calibrating marker proteins. The position of hIFNγ is indicated wit arrow heads. The bottom table contains the number of biologically active units that was found in the respective fractions.

In these experiments with the eukaryotic proteins human interferon-γ and murine interleukin-2, two proteins which do aggregate readily in *E. coli*, less heterologous protein is formed after the IPTG induction at low temperature (FIG. 5A). However, the high expression at 42° C. results exclusively in the forming of inclusion bodies, while after IPTG induction at 28° C. a significant quantity of soluble protein is produced (FIGS. 6A and 6B). The soluble protein fraction visible on gel corresponds with the obtained amount of activity after a biological titration.

Example 4

Use of the Ant-based Induction System from Different Replicons

In a preferred embodiment of the invention the synthesis of the repressor, the antirepressor and the repressor of the promoter controlling the gene of the antirepressor takes place from a low copy number plasmid. This example illustrates the use of the ant system from other replicons.

Figure 7A:
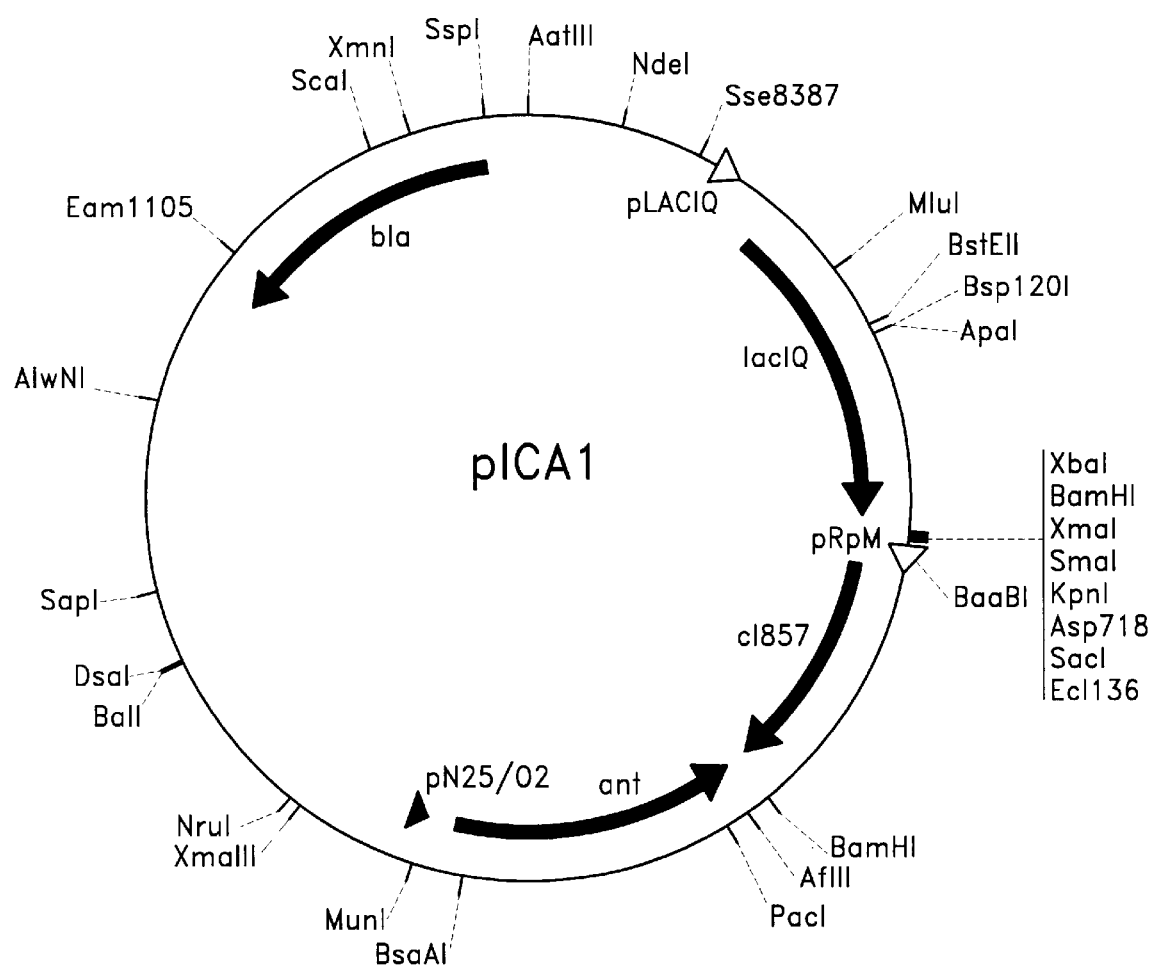
FIG. 7A: Schematic drawing of the pICA1 plasmid comprising the lactose repressor gene (lacI) controlled by the lacIq promoter, the thermosensitive lambda repressor gene (cI857) controlled by the lambda PM promoter (overlapping the opposite oriented PR promoter), and the P22 antirepressor gene (ant) fused to a promoter that is controlled by the lactose repressor (PN25/O2). The plasmid further comprises the high-copy replication origin derived from ColE1, and a gene for γ-lactamase (bla) for ampicilin resistance. Some restriction enzyme recognition sites are indicated.
Figure 7B:
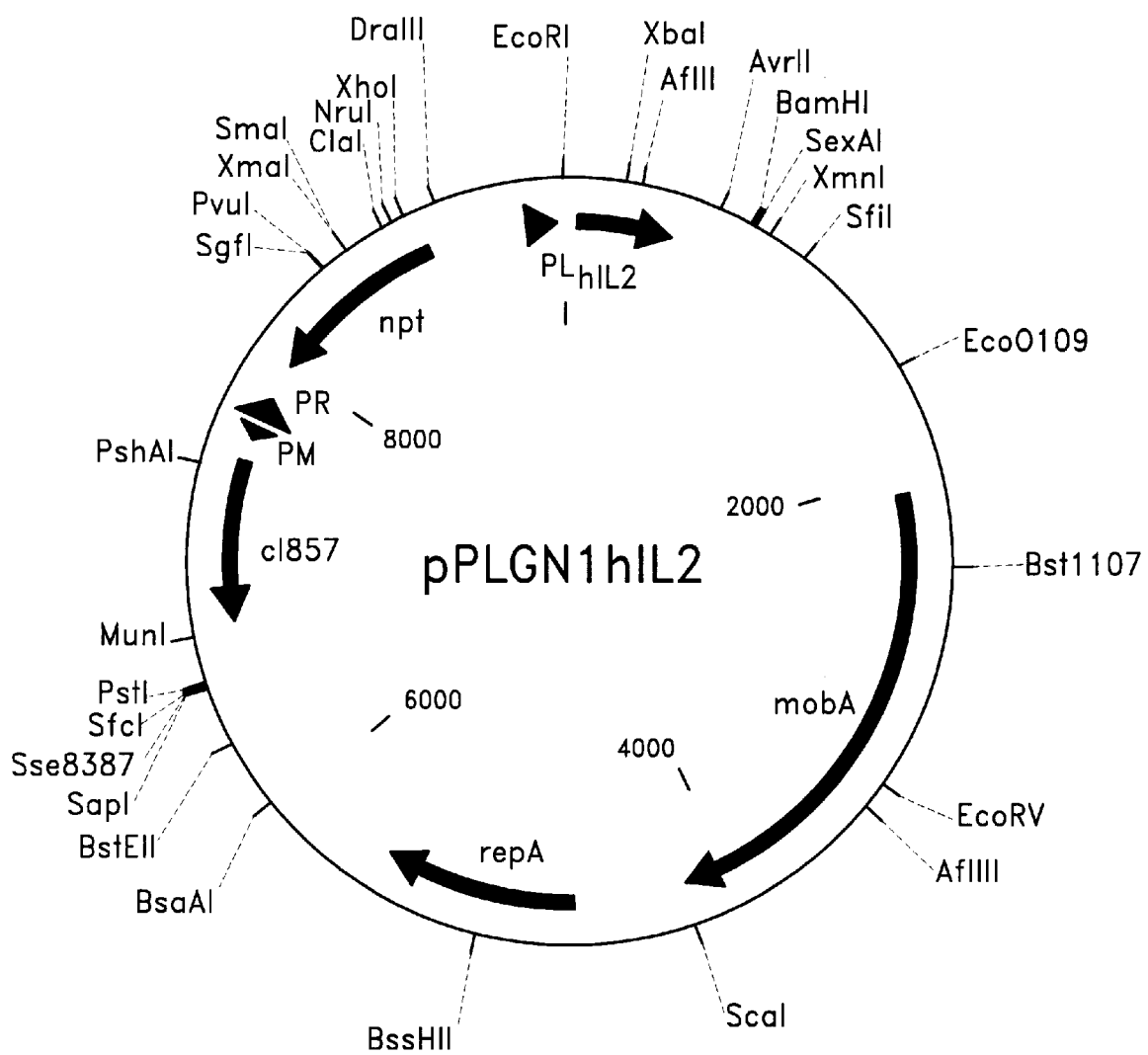
FIG. 7B: Schematic drawing of the pPLGN1hIL2 plasmid comprising the lambda PL promoter functionally coupled to the gene encoding human interleukin 2 (hIL2). The plasmid further comprises the lambda repressor cI857 gene, a broad host range replication origin derived from PRSF1010, and a gene for neomycin phosphotransferase, for kanamycin resistance. Some restriction enzyme recognition sites are indicated.

As the case arises, the regulatory genes (repressor cI857 controlled by the auto-regulatory promoter $P_M$, antirepressor ant controlled by the $P_{N25/O2}$ promoter and the lacI gene controlled by the constitutive $P_{lacI}^q$-promoter) were induced from a high copy number plasmid and a ColE1/pMB1 replication origin (FIG. 7A). The gene for expressing (human interleukin 2, hIL2) was linked on a plasmid with a high copy number and a broad host range to the $\lambda P_L$ promoter and a prokaryote ribosome binding site (originating from the ner gene of phage Mu). This plasmid also contains an extra copy of the $\lambda P_L$ repressor gene cI857. The pPLGNIhIL2 plasmid also contains the required functions also enabling replication in other bacteria (FIG. 7B).

Figure 7C:
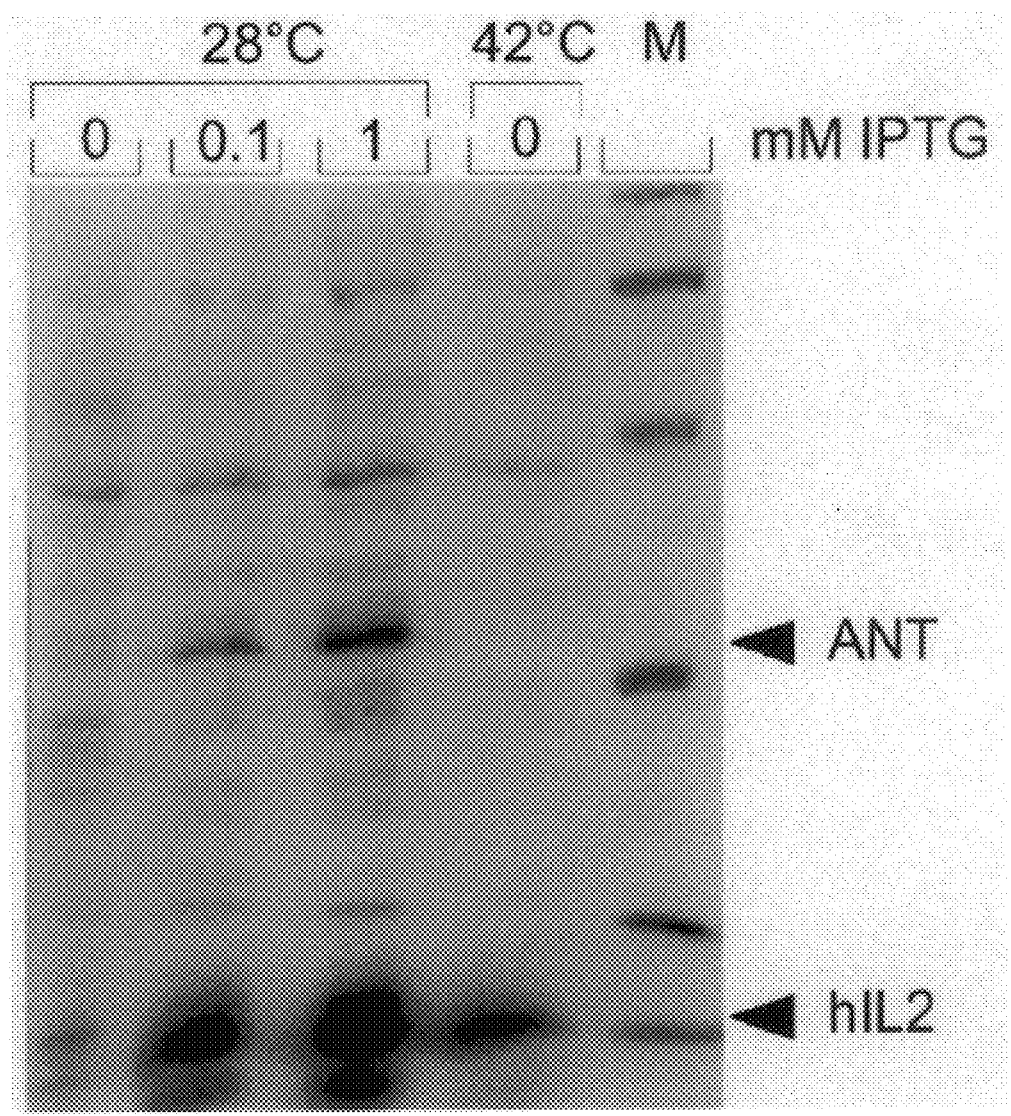
FIG. 7C: Coomassie Brillant Blue stained protein gel comparing protein extracts from MC1061 [pICA1] [pPLGN1hIL2] at 28° C. after the addition of 0, 0.1 or 1 mM IPTG, or after shifting the bacteria to 42° C. The position of ant and hIL2 is indicated with an arrow head.

Induction was investigated after adding 0, 0.1 or 1 mM of the inducer IPTG, which provides induction of ant from the $P_{N25/O2}$ promoter, which in turn brings about inhibition of the $\lambda P_L$, repressor cI857 and thus activates the $\lambda P_L$ which results in overexpression of, in this case, hIL2 (FIG. 7C). These inductions were carried out at 28° C. and compared with the classic temperature deactivation of cI857 by growing the bacteria further at 42° C.

In this example the relative production of hIL2 using the ant system and by temperature induction are roughly equal. The temperature induction at 42° C. was however found to cause a greater growth-inhibiting effect (the gel shows equivalent samples of culture medium).

Example 5

An Ant-based Expression System for the Lambdoid Promoters P22P$_L$ and P22P$_R$ Induction of a repressor antagonist in order to induce a promoter can in principle also be applied to promoters other than the $\lambda P_L$. In this example a vector system is described which makes use of the P22 ant gene to deactivate the homologous P22c2 repressor and thus obtain induction of the P22P$_L$ or the P22P$_R$.

Figure 8A:
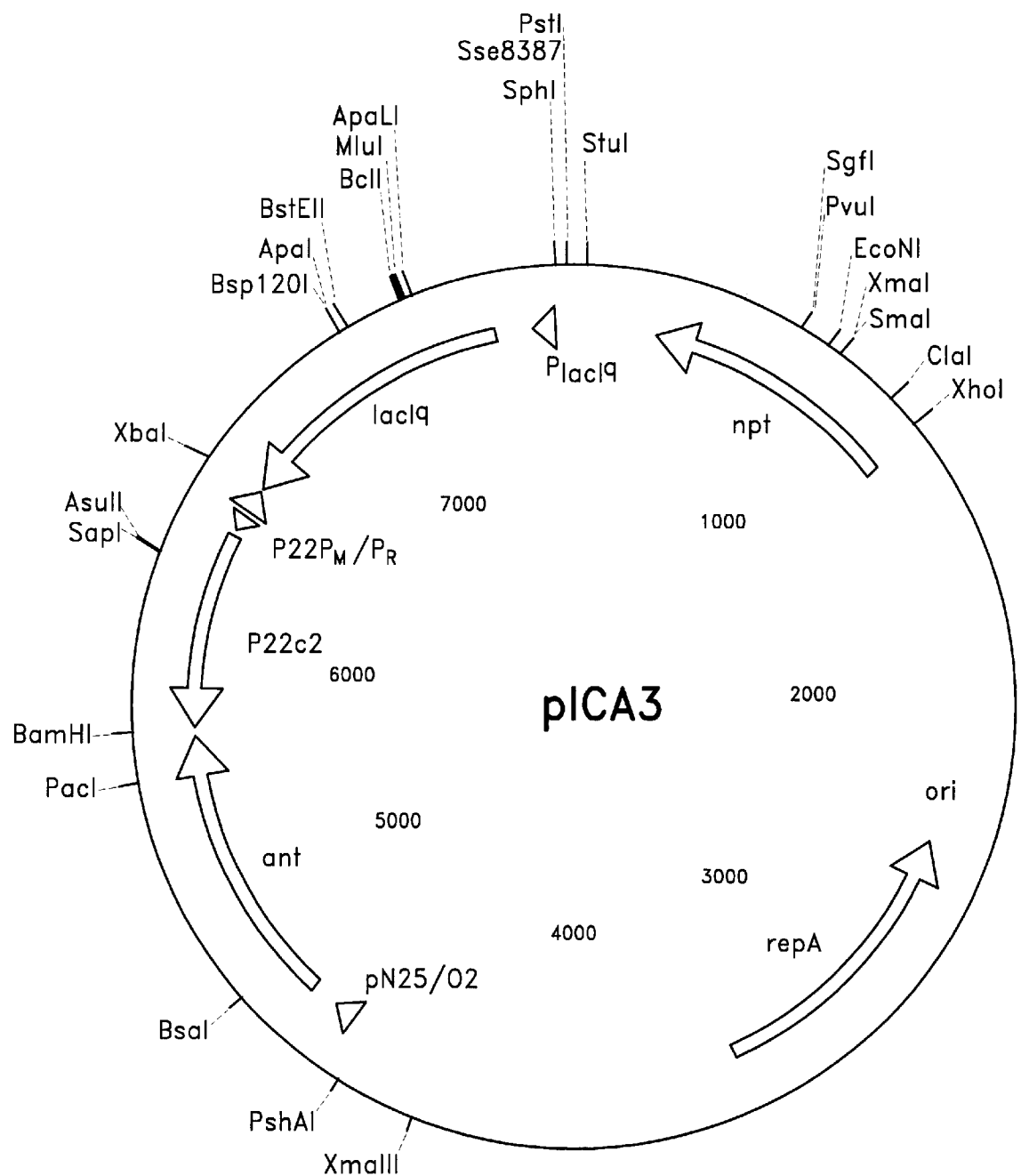
FIG. 8A: Schematic drawing of the pICA3 plasmid comprising the lactose repressor gene (lacI) controlled by the lacIq promoter, the P22 repressor gene c2 controlled by the P22 PM promoter (overlapping the opposite oriented P22PR promoter), and the P22 antirepressor gene (ant) fused to a promoter that is controlled by the lactose repressor (PN25/O2). The plasmid further comprises the low-copy replication origin derived from pLG339, and a neomycin phosphotransferase gene (npt) for kanamycin resistance. Some restriction enzyme recognition sites are indicated.
Figure 8B:
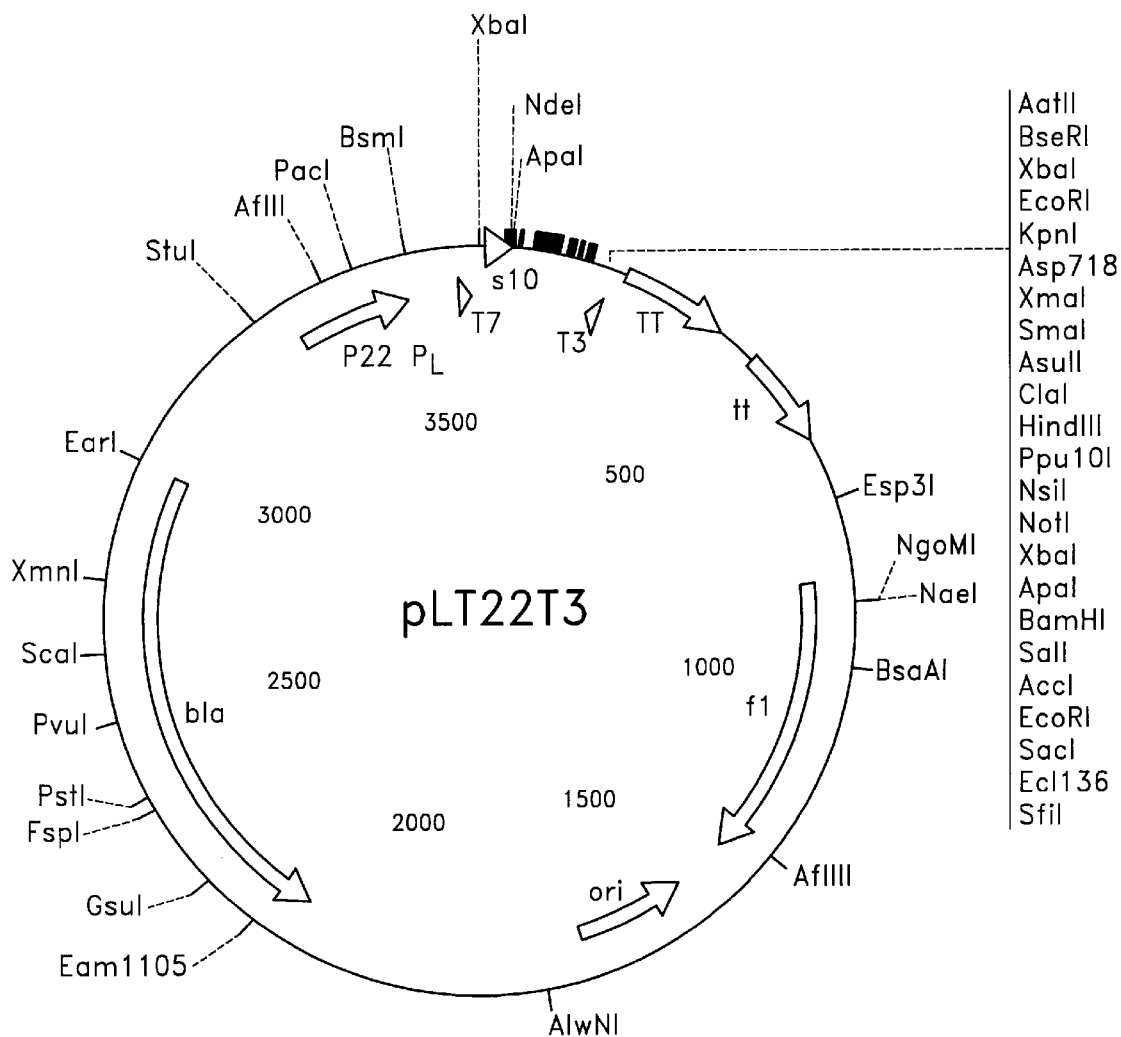
FIG. 8B: Schematic drawing of a typical expression plasmid that can be combined wit pICA3. The plasmid contains the same features as pLT10T3 (FIG. 1B), but now contains the P22 PL promoter instead of the lambda PL promoter.
Figure 8C:
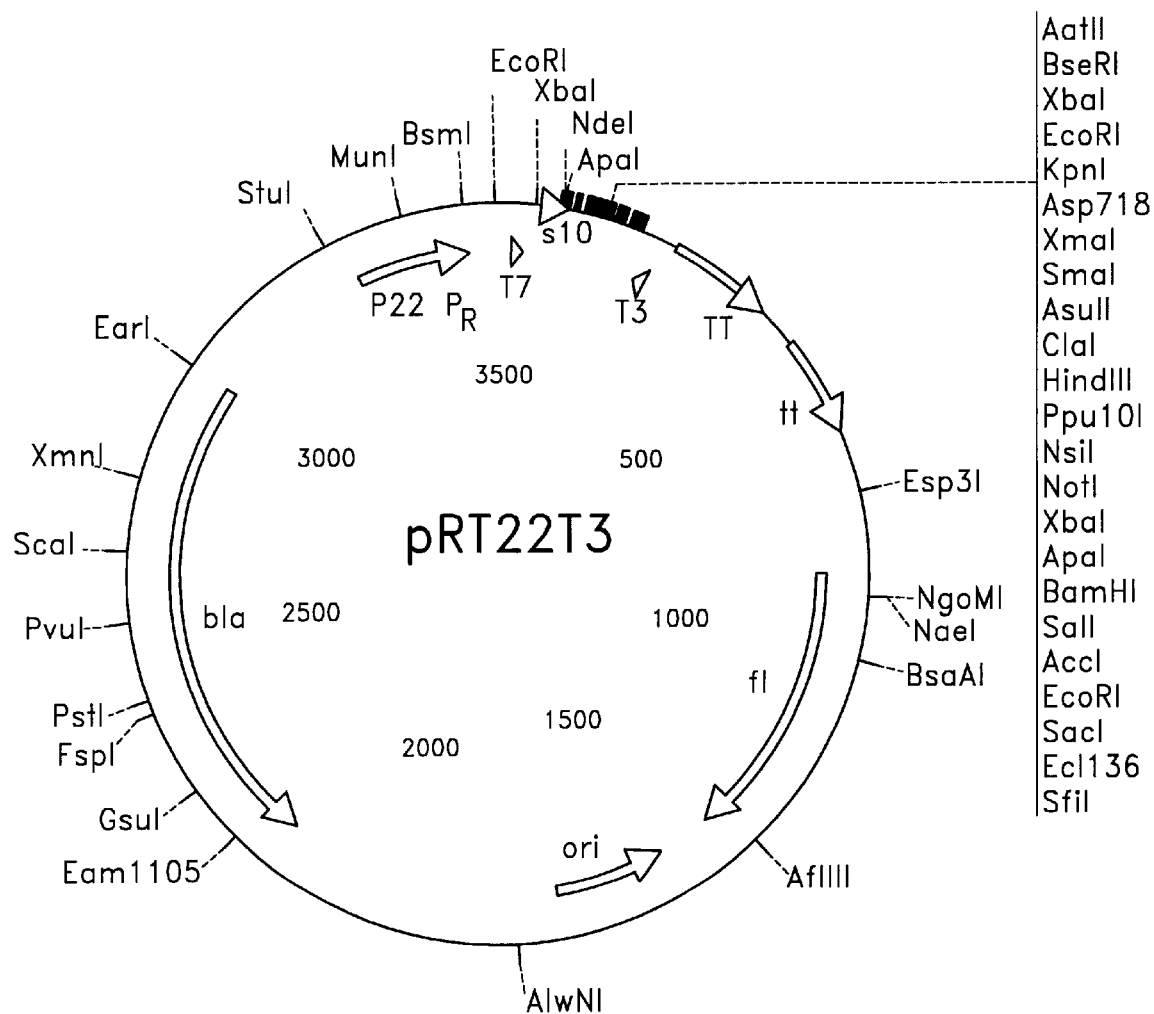
FIG. 8C: Schematic drawing of a typical expression plasmid that can be combined wit pICA3. The plasmid contains the same features as pLT10T3 (FIG. 1B), but now contains the P22 PR promoter instead of the lambda PL promoter.

Constructed first for this purpose was the pICA3 plasmid which is a derivative of pICA2 but which contains the P22c2 repressor gene instead of the $\lambda$cI857 repressor gene. The $\lambda P_L$ promoter in pLt10T3 was further replaced by both the P22P$_L$ (pLT22T3) and the P22P$_R$ (pRT22T3). Both pICA3 and pLT22T3 and pRT22T3 are shown in FIG. 8.

Example 6

An Ant-based Regulatory System for $\lambda P_L$ and $\lambda P_R$ that is Inducible with L-arabinose In the pICA2 regulatory plasmid, the induction of ant is controlled by the IPTG-inducible $P_{T5\ N25/O2}$. Control of ant-gene expression can in principle come from any inducible promoter. It is preferred that the promoter of choice is inducible also at lower temperatures (28° C. or lower). It is also preferred that the promoter of choice be well regulated. If this would not be the case, the level of expression of the uninduced culture can be sufficient to initiate continuous expression. Uncontrolled expression is likely to result in eventual loss of the functional expression strain.

In this example a regulatory plasmid was constructed containing the promoter region of the E. coli arabinose operon ($P_{araBAD}$) and the gene encoding the araC repressor of this promoter. The ant-gene is in this way controlled by a promoter which is inducible by the addition of L-arabinose.

Figure 9:
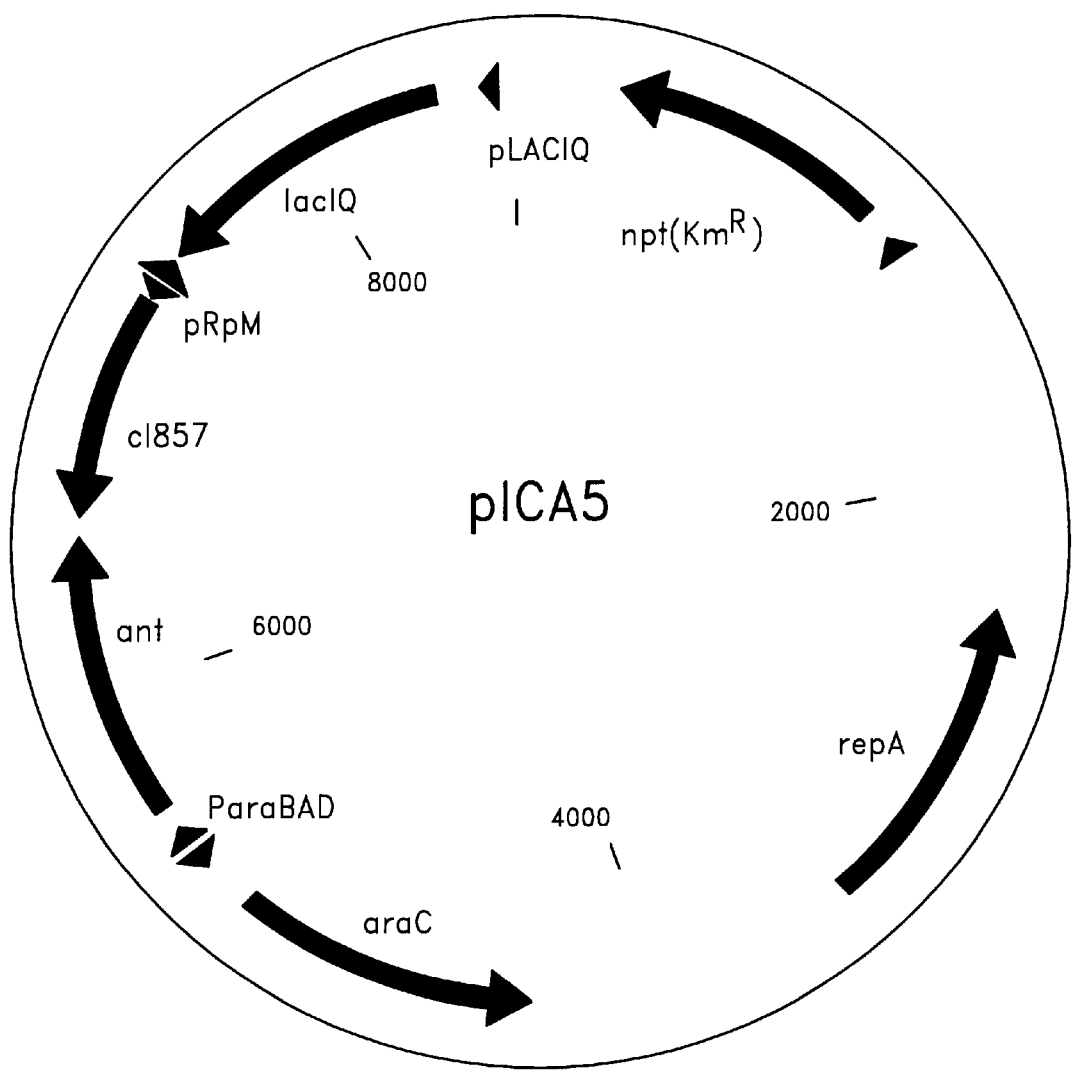
FIG. 9: Schematic drawing of the pICA5 plasmid comprising the lactose repressor gene (lacI) controlled by the lacIq promoter, the thermosensitive lambda repressor gene (cI857) controlled by the lambda PM promoter (overlapping the opposite oriented PR promoter), and the P22 antirepressor gene (ant) fused to a promoter that is controlled by the arabinose repressor (ParaBAD), and the repressor gene for the arabinose promoter (araC). The plasmid further comprises the low-copy replication origin derived from pLG339, and a neomiycin phosphotransferase gene (npt) for kanamycin resistance.

The ParaBAD promoter and the araC repressor gene encoding the repressor for this promoter were amplified from a wild type E. coli K12 bacterial strain, using the PCR primers NM73 (ATATATCCAAGGTTATGCAATCGCCA-TCGTTTCACTCC) (SEQ. ID NO: 3) and NM72 ATATCG-GCCGTTATGACAACTTGACGGCTACATC (SEQ. ID NO: 4). PCR amplification was performed with Vent DNA polymerase (New England Biolabs) and the resulting fragment was cloned between the XmaIII and the StyI restriction sites present in pICA2. The resulting pICA5 plasmid was characterized by restriction site mapping, PCR analysis and the PCR amplified insert was sequenced. FIG. 9 shows the pICA5 plasmid.

Example 7

Comparison of the $\lambda P_L$-ant Induction System with Other IPTG Inducible Expression Systems Although the $\lambda P_L$ promoter is amongst the strongest promoters recognized by the E. coli transcriptional machinery, the T7 promoter, which is recognized by the extremely active T7 RNA-polymerase (T7RNAP), allows for a far greater amount of mRNA to be formed (Studier and Moffatt, 1986). A well-controlled, IPTG-based induction system for the T7RNAP that also resides on a pSC101-derived low-copy number plasmid system was previously described (Mertens et al., 1995b). The pLT10mIL2T and the pLT10hIFNγT expression plasmids were used, which contain both the $\lambda$PL and the $P_{T7}$ promoters (Mertens et al., 1995a), to compare the expression obtained from either the $P_{T7}$ and the $\lambda P_L$ induction system upon addition of IPTG (FIG. 10A).

Strikingly, cells containing the T7-based induction system stopped growing almost immediately after induction, while those induced by the $\lambda P_L$-ant system continued to proliferate. This resulted in an almost 10-fold higher biomass after 4 h of induction at 28° C. Remarkably, after induction of the $P_{T7}$T7RNAP system all of the mIL2 and almost all of the hIFNγ were in the insoluble phase, while when using the $\lambda P_L$-ant system about 50% of the heterologous protein was found in the soluble phase.

The coding sequence of hIFNγ combined with the strong RBST7g10 resulted in a favorable translation initiation region (Mertens et al., 1995a). When combined with a strong promoter on a high-copy number plasmid, abundant expression was obtained after induction. To emphasize the difference in promoter strength between various IPTG-inducible promoters such as $P_{trc}$ (Amann et al., 1988), $P_{T5\ N25/O2}$ (St über et al., 1984) and $P_{T7}$ (Mertens et al., 1995b; Studier et al., 1990) and the $\lambda P_L$-ant system, the RBS-gene-terminator combination combined with the aforementioned promoters was transferred to an RK2 replicon (Blatny et al., 1997). This resulted in expression plasmids with a much lower copy-number than the normally used ColE1-derived vectors. Subsequently the induction of hIFNγ was then compared using these vectors. Using the stronger $P_{T7}$ resulted in a higher level of production, but all of the hIFNγ produced was insoluble. Employing the $P_{trc}$ and $P_{T5\ N25/O2}$ promoters did not result in visually detectable levels of induced protein from this low-copy number vector after SDS-PAGE staining with Coomassie Brilliant Blue. However, when the $\lambda P_L$-ant system was used a clearly detectable level of huIFNγ was synthesized, while the protein remained completely soluble (FIG. 10B).

Figure 10A:
FIG. 10A: Coomassie Brillant Blue stained protein gel comparing soluble (S) and non-soluble (pellet) (P) protein extracts from MC1061[pT7POL26][pLT10mIL2T], MC1061[pT7POL26][pLT10hIFNGT], MC1061[pICA2][pLT 10mIL2T] and MC1061[pICA2][pLT10hIFNGT], all induced with 1 mM IPTG at 28° C. The position of murine interleukin 2 (mIL2) and human interferon gamma (hIFNγ) is indicated with an arrow head.

FIG. 10 shows that induction at 28° C. using the $\lambda P_L$/ant system is more efficient in producing functional protein than other IPTG-inducible expression systems. FIG. 10A demonstrates the SDS-PAGE analysis of soluble (S) and pelleted (P) proteins after induction of pLT10mIL2T or pLT10hIFNγT in either MC1061 [pT7POL26] (inducing the T7 promoter) or MC1061 [pICA2] (inducing the $\lambda P_L$-promoter). Induction was obtained by growing for 5 h at 28° C. in the presence of IPTG. Clearly, more soluble mIL2 was obtained by using the $\lambda P_L$/ant induction system. Unlike the T7-system, the latter system also allowed the cultures to continue growing, and thus resulted in a higher biomass accumulation.

Figure 10B:
FIG. 10B: Coomassie Brillant Blue stained protein gel comparing soluble (S) and non-soluble (pellet) (P) protein extracts from MC1061 strains containing the hIFNγ expression module on a pRK2 replicon, controlled by the T7 polymerase promoter (PT7), the PN25/O2 promoter (PN25), the trc promoter (Ptrc) and an ant-controlled lambda PL promoter (PL/ant). Bacteria were grown at 28° C. and induced with 1 mM IPTG. The position of human interferon gamma (hIFNγ) is indicated with an arrow head.

FIG. 10B is a comparison of expression of the RBS$_{T7g10}$-hFNγ-T7Tφ module combined with some different IPTG-inducible promoters on an RK2-derived low-copy number plasmid. (S=soluble, P=pelleted fraction). Arrow points indicate the position of the induced proteins. Protein markers (M) are 94; 67; 43; 30; 21 and 14 kDa.

REFERENCES

Amann et al. (1988). Tightly regulated tac promoter vectors useful for the expression of unfused and fused proteins in *E. coli*. Gene 69, 301–315.

Bishia, W. R., Rappuoli, R., and Murphy, J. R. (1987). High-level expression of a proteolytically sensitive diphtheria toxin fragment in *Escherichia coli*. J. Bacteriol. 169, 5140–5151.

Blatny et al. (1997) Improved broad-host-range RK2 vectors useful for high and low regulated gene expression levels in gram-negative bacteria. Plasmid 38, 35–51.

Casadaban, M. J. and Cohen, S. N. (1980). Analysis of gene control signals by DNA fusion and cloning in *Escherichia coli*. J. Mol. Biol. 138, 179–207.

Devos, R., Cheroutre, H., Taya, Y., and Fiers, W. (1982). Isolation and characterisation of IFN-gamma MRNA derived from mitogen-induced human spienocytes. J. Interferon Res. 2, 409–420.

Guisez, Y., Demolder, J., Mertens, N., Raeymaekers, A., Plaetinck, G., Robbens, J., Vandekerckhove, J., Remaut, E., and Fiers, W. (1993). Highlevel expression, purification, and renaturation of recombinant murine interleukin-2 from *Escherichia coli*. Protein Expr. Purif 4, 240–246.

Knaus, R. and Bujard, H. (1988). PL of coliphage lambda: an alternative solution foran efficient promoter. EMBO J. 7, 2919–2923.

Lanzer, M. and Bujard, H. (1988). Promoters largely determine the efficiency of repressor action. Proc. Natl. Acad. Sci. U.S.A. 85, 8973–8977.

Lin, K., Kurland, I., Xu, L. Z., Lange, A. J., Pilkis, J., el Maghrabi, M. R., and Pilkis, S. J. (1990). Expression of mammalian liver glycolyticlgiuconeogenic enzymes in *Escherichia coli*: recovery of active enzyme is strain and temperature dependent. Protein Expr. Purif 1, 169–176.

Mertens, N., Remaut, E., and Fiers, W. (1995a). A tight transcriptional control ensures stable high-level expression from T7 promoter-based expression plasmids. Bio/Technology 13, 175–179.

Mertens, N., Remaut, E., and Fiers, W. (1995b). Versatile, multi-featured vectors for high-level expression of heterologous genes in *E. coli*: overproduction of human and murine cytokines. Gene 164, 9–15.

Miller, J. (1972). Experiments in Molecular Genetics (NY: Cold Spring Harbor Laboratory).

Mizukami, T., Komatsu, Y., Hosoi, N., Ito, S., and Oka, T. (1986). Production of active human interferon-γ in *E. coli*, 1. Preferential production by lower culture temperature. Biotechnol. Letters 8, 605–610.

Remaut, E., Tsao, H., and Fiers, W. (1983b). Improved plasmid vectors with a thermoinducible expression and temperature-regulated runaway replication. Gene 22, 103–113.

Sambrook, J., Fritsch, E. F., and Maniatis, T. (1989). Molecular Cloning: a Laboratory Manual. Cold Spring Harbor Laboratory Press, Cold Spring Harbor.

Sauer, R. T., Krovatin, W., DeAnda, J., Youderian, P., and Susskind, M. M. (1983). Primary structure of the immI immunity region of bacteriophage P22.

Sauer, R. T., Krovatin, W., DeAnda, J., Youderian, P., and Susskind, M. M. (1983). Primary structure of the immI immunity region of bacteriophage P22. J. Mol. Biol. 168, 699–713.

Schein, C. H. and Noteborn, M. H. M. (1988). Formation of soluble recombinant proteins in *E. coli* is favored by lower growth temperature. Bio/Technology 6, 291–294.

Shirano, Y. and Shibata, D. (1990). Low temperature cultivation of Escherichia coli carrying a rice lipoxygenase L-2 CDNA produces a soluble and active enzyme at a high level. Febs. Lett. 271, 128–130.

Stoker, N. G., Fairweather, N. F., and Spratt, B. G. (1982). Versatile low copy-number vectors for cloning in *E. coli*. Gene 18, 335–341.

Stueber, D., Ibrahimi, I., Cutler, D., Dobberstein, B., and Bujard, H. (1984). A novel in vitro transcription-translation system: accurate and efficient synthesis of single proteins from cloned DNA sequences. EMBO J. 3, 3143–3148.

Studier and Moffatt (1986) Use of bacteriophage T7RNA polymerase to direct selective high level expression of cloned genes. J. Mol. Biol. 189, 113–130.

Studier et al. (1990) Use of T7RNA polymerase to direct expression of cloned genes. Methods Enzymol. 185, 60–89.

What is claimed is:

1. The polynucleotide components for inducible expression of a gene or genes of interest (GOI) comprising:
   a lambdoid promoter operably linked to said GOI, said lambdoid promoter being under control of a repressor,
   a gene coding for said repressor,
   a gene coding for an antirepressor of the repressor, wherein said antirepressor binds to the repressor and wherein said antirepressor is the ant protein of lambdoid phage p22; and
   an inducible promoter regulating the expression of said antirepressor.

2. The polynucleotide components claimed in claim 1, wherein said inducible promoter is a promoter originating from a gene which is not the antirepressor gene.

3. The polynucleotide components as claimed in claim 2, wherein said inducible promoter is $P_{N25/O2}$.

4. The polynucleotide components as claimed in claim 1, wherein the repressor is the lacI repressor of *E. coli*.

5. The polynucleotide components as claimed in claim 1, wherein the components are on a plurality of replicons.

6. An isolated regulatory replicon, comprising a gene coding for the ant protein of lambdoid phage p22, wherein said gene coding for the ant protein of lambdoid phage p22 is under the control of an inducible promoter, and wherein said ant protein of lambdoid phage p22 represses the action of a repressor of a lambdoid promoter by binding to the repressor; and said regulatory replicon further comprising a lambdoid promoter operatively linked to a GOI; wherein said gene coding for the ant protein of lambdoid phage p22, the gene encoding said repressor of the lambdoid promoter, and the gene of interest (GOI) are comprised within three separate operons.

7. The regulatory replicon as claimed in claim 6, wherein said inducible promoter originates from a gene other than the antirepressor gene.

8. The regulatory replicon as claimed in claim 6, further comprising a gene coding for a repressor of said inducible promoter of the antirepressor gene.

9. The regulatory replicon as claimed in claim 8, wherein said antirepressor is the lambdoid phage P22 ant protein, wherein said inducible promoter is the PN25/O2 promoter, wherein said repressor of said inducible promoter is the lacIq protein encoded by the lacIq gene, wherein the lacIq gene is under the control of the pLacIq promoter and wherein said repressor of said lambdoid promoter is the cI857 repressor.

10. The regulatory replicon as claimed in claim 9, wherein said regulatory replicon is the plasmid pICA2.

11. A polynucleotide comprising a regulatory replicon as claimed in claim 8, and further comprising an expression vector comprising a gene or genes of interest under the control of a lambdoid promoter.

12. A method for producing a gene product in a heterologous host, comprising:
   providing a culture of a host comprising a heterologous sequence which codes for the gene product, wherein the expression of the heterologous sequence is under the control of a regulation system, said regulation system comprising: a lambdoid promoter operably linked to the heterologous sequence, a gene coding for a repressor for the lambdoid promoter and a gene coding for an antirepressor, wherein said antirepressor gene is operably linked to an inducible promoter and wherein said antirepressor is the ant protein of lambdoid phage p22; and
   adding an inducer for said inducible promoter of said antirepressor gene.

13. The method as claimed in claim 12, wherein said inducible promoter of the antirepressor gene is the $P_{N25/O2}$ promoter and said inducer is IPTG.

* * * * *